(12) United States Patent
Malandain et al.

(10) Patent No.: US 8,105,236 B2
(45) Date of Patent: Jan. 31, 2012

(54) SURGICAL ACCESS DEVICE, SYSTEM, AND METHODS OF USE

(75) Inventors: Hugues F. Malandain, Mountain View, CA (US); Derek Rothwell, Los Altos, CA (US); Avram Allan Edidin, Portola Valley, CA (US)

(73) Assignee: Kyphon Sarl, Neuchatel (CH)

( * ) Notice: Subject to any disclaimer, the term of this patent is extended or adjusted under 35 U.S.C. 154(b) by 692 days.

(21) Appl. No.: 11/448,228

(22) Filed: Jun. 7, 2006

(65) Prior Publication Data

US 2007/0010716 A1 Jan. 11, 2007

Related U.S. Application Data

(60) Provisional application No. 60/698,430, filed on Jul. 11, 2005.

(51) Int. Cl.
*A61B 1/32* (2006.01)

(52) U.S. Cl. ......... 600/219; 600/206

(58) Field of Classification Search ......... 600/224, 600/219, 223, 207, 222, 221
See application file for complete search history.

(56) References Cited

U.S. PATENT DOCUMENTS

| | | | | |
|---|---|---|---|---|
| 2,083,573 A | * | 6/1937 | Morgan | 600/224 |
| 2,296,793 A | * | 9/1942 | Kirschbaum | 600/210 |
| 3,998,217 A | | 12/1976 | Trumbull et al. | |
| 4,130,113 A | * | 12/1978 | Graham | 600/224 |
| 4,429,691 A | | 2/1984 | Niwa et al. | |
| 4,904,257 A | | 2/1990 | Mori et al. | |
| 4,969,888 A | | 11/1990 | Scholten et al. | |
| 5,125,396 A | | 6/1992 | Ray | |
| 5,163,949 A | | 11/1992 | Bonutti | |
| 5,331,975 A | | 7/1994 | Bonutti | |
| 5,667,520 A | | 9/1997 | Bonutti | |
| 5,685,826 A | | 11/1997 | Bonutti | |
| 5,688,223 A | * | 11/1997 | Rosendahl | 600/215 |
| 5,707,390 A | | 1/1998 | Bonutti | |
| 5,716,325 A | | 2/1998 | Bonutti | |

(Continued)

FOREIGN PATENT DOCUMENTS

EP            455282 A2 * 11/1991

(Continued)

OTHER PUBLICATIONS

Schreiber et al., Percutaneous Nucleotomy: Technique With Discoscopy, Orthopedics, Apr. 1991, p. 439-444, vol. 14.

(Continued)

*Primary Examiner* — Thomas C. Barrett
*Assistant Examiner* — David Bates

(57) ABSTRACT

A surgical access device can include a plurality of retractor members that together define a lumen having a first cross-sectional dimension. Each of the plurality of retractor members can be moved radially outward to at least a second cross-sectional dimension to create a surgical access passage. The surgical access device, systems and kits comprising the surgical access device, and methods of using the surgical access device can include a mechanism for inserting an elongate member from exterior the body to the surgical site, a mechanism for moving the retractor members radially outward, a mechanism for guiding the radially outward movement of the retractor members, a mechanism for securing each of the retractor members in a range of positions, and a mechanism for illuminating the surgical site. Variations of the devices, systems, kits, and methods are useful for creating and maintaining a surgical access passage for performing minimally invasive surgery.

13 Claims, 14 Drawing Sheets

U.S. PATENT DOCUMENTS

| | | | |
|---|---|---|---|
| 5,785,648 A * | 7/1998 | Min | 600/206 |
| 5,792,044 A * | 8/1998 | Foley et al. | 600/114 |
| 5,928,139 A | 7/1999 | Koros et al. | |
| 5,967,970 A * | 10/1999 | Cowan et al. | 600/207 |
| 5,972,015 A | 10/1999 | Scribner et al. | |
| 6,004,341 A | 12/1999 | Zhu et al. | |
| 6,042,596 A | 3/2000 | Bonutti | |
| 6,048,346 A | 4/2000 | Reiley et al. | |
| 6,066,154 A | 5/2000 | Reiley et al. | |
| 6,083,154 A | 7/2000 | Liu et al. | |
| 6,187,000 B1 | 2/2001 | Davison et al. | |
| 6,206,826 B1 | 3/2001 | Mathews et al. | |
| D439,980 S | 4/2001 | Reiley et al. | |
| 6,213,940 B1 * | 4/2001 | Sherts et al. | 600/231 |
| 6,235,043 B1 | 5/2001 | Reiley et al. | |
| 6,241,734 B1 | 6/2001 | Scribner et al. | |
| 6,248,110 B1 | 6/2001 | Reiley et al. | |
| 6,254,533 B1 | 7/2001 | Fadem et al. | |
| 6,280,456 B1 | 8/2001 | Scribner et al. | |
| D449,691 S | 10/2001 | Reiley et al. | |
| 6,423,083 B2 | 7/2002 | Reiley et al. | |
| 6,425,859 B1 | 7/2002 | Foley et al. | |
| 6,440,138 B1 | 8/2002 | Reiley et al. | |
| 6,468,279 B1 | 10/2002 | Reo | |
| D467,657 S | 12/2002 | Scribner | |
| D469,871 S | 2/2003 | Sand | |
| 6,575,919 B1 | 6/2003 | Reiley et al. | |
| 6,579,532 B1 | 6/2003 | Mandel et al. | |
| 6,607,544 B1 | 8/2003 | Boucher et al. | |
| 6,613,054 B2 | 9/2003 | Scribner et al. | |
| 6,620,181 B1 | 9/2003 | Bonutti | |
| 6,623,505 B2 | 9/2003 | Scribner et al. | |
| 6,632,235 B2 | 10/2003 | Weikel et al. | |
| D482,787 S | 11/2003 | Reiss | |
| 6,641,587 B2 | 11/2003 | Scribner et al. | |
| 6,645,213 B2 | 11/2003 | Sand et al. | |
| D483,495 S | 12/2003 | Sand | |
| 6,663,647 B2 | 12/2003 | Reiley et al. | |
| 6,679,886 B2 | 1/2004 | Weikel et al. | |
| 6,716,216 B1 | 4/2004 | Boucher et al. | |
| 6,719,761 B1 | 4/2004 | Reiley et al. | |
| 6,719,773 B1 | 4/2004 | Boucher et al. | |
| 6,726,691 B2 | 4/2004 | Osorio et al. | |
| 6,740,093 B2 | 5/2004 | Hochschuler et al. | |
| 6,800,084 B2 | 10/2004 | Davison et al. | |
| 6,814,736 B2 | 11/2004 | Reiley et al. | |
| 6,887,246 B2 | 5/2005 | Bhatnagar et al. | |
| 6,945,933 B2 | 9/2005 | Branch et al. | |
| 7,022,082 B2 * | 4/2006 | Sonek | 600/461 |
| 7,081,122 B1 * | 7/2006 | Reiley et al. | 606/185 |
| 7,083,621 B2 | 8/2006 | Shaolian et al. | |
| 7,195,592 B2 * | 3/2007 | Ravikumar et al. | 600/219 |
| 7,223,233 B2 | 5/2007 | Branch et al. | |
| 7,427,264 B2 | 9/2008 | Nowitzke et al. | |
| 2002/0002324 A1 | 1/2002 | McManus | |
| 2002/0022856 A1 | 2/2002 | Johnson et al. | |
| 2002/0026195 A1 | 2/2002 | Layne et al. | |
| 2002/0032447 A1 | 3/2002 | Weikel et al. | |
| 2002/0058947 A1 | 5/2002 | Hochschuler et al. | |
| 2002/0058957 A1 | 5/2002 | Farascioni | |
| 2002/0099384 A1 | 7/2002 | Scribner et al. | |
| 2002/0161373 A1 | 10/2002 | Osorio et al. | |
| 2002/0177866 A1 | 11/2002 | Weikel et al. | |
| 2003/0004530 A1 | 1/2003 | Reo | |
| 2003/0032963 A1 | 2/2003 | Reiss et al. | |
| 2003/0050644 A1 | 3/2003 | Boucher et al. | |
| 2003/0191414 A1 | 10/2003 | Reiley et al. | |
| 2004/0010260 A1 | 1/2004 | Scribner et al. | |
| 2004/0049203 A1 | 3/2004 | Scribner et al. | |
| 2004/0054353 A1 | 3/2004 | Taylor | |
| 2004/0133208 A1 | 7/2004 | Weikel et al. | |
| 2004/0133280 A1 | 7/2004 | Trieu | |
| 2004/0143169 A1 | 7/2004 | Branch et al. | |
| 2004/0210297 A1 | 10/2004 | Lin et al. | |
| 2004/0215344 A1 | 10/2004 | Hochschuler et al. | |
| 2004/0225296 A1 | 11/2004 | Reiss et al. | |
| 2005/0090852 A1 | 4/2005 | Layne et al. | |
| 2005/0124999 A1 | 6/2005 | Teitelbaum et al. | |
| 2005/0159651 A1 * | 7/2005 | Raymond et al. | 600/213 |
| 2005/0215866 A1 * | 9/2005 | Kim | 600/233 |
| 2005/0234304 A1 | 10/2005 | Dewey et al. | |
| 2006/0052672 A1 * | 3/2006 | Landry et al. | 600/233 |
| 2006/0058791 A1 | 3/2006 | Broman et al. | |
| 2006/0058884 A1 | 3/2006 | Aram et al. | |
| 2006/0069404 A1 * | 3/2006 | Shluzas et al. | 606/198 |
| 2006/0074278 A1 * | 4/2006 | Petit et al. | 600/224 |
| 2006/0116689 A1 | 6/2006 | Albans et al. | |
| 2006/0116766 A1 | 6/2006 | Lemaire | |
| 2006/0122614 A1 | 6/2006 | Truckai et al. | |
| 2006/0122622 A1 | 6/2006 | Truckai et al. | |
| 2006/0122623 A1 | 6/2006 | Truckai et al. | |
| 2006/0122624 A1 | 6/2006 | Truckai et al. | |
| 2006/0122704 A1 | 6/2006 | Vresilovic et al. | |
| 2006/0149379 A1 | 7/2006 | Kuslich et al. | |
| 2006/0224044 A1 * | 10/2006 | Marchek et al. | 600/233 |
| 2007/0010708 A1 * | 1/2007 | Ness | 600/115 |
| 2007/0118023 A1 * | 5/2007 | Smith et al. | 600/219 |

FOREIGN PATENT DOCUMENTS

| | | |
|---|---|---|
| WO | WO 93/25148 | 12/1993 |
| WO | WO 98/56301 | 12/1998 |
| WO | WO 00/44319 | 8/2000 |
| WO | WO 2005/023085 A2 | 3/2005 |
| WO | WO 2005/027726 A2 | 3/2005 |
| WO | WO 2005/030318 A1 | 4/2005 |

OTHER PUBLICATIONS

U.S. Appl. No. 11/056,785, filed Feb. 11, 2005, Markworth et al.

Bhan, S. et al., "Percutaneous Bone Grafting for Nonunion and Delayed Union of Fractures of the Tibial Shaft," International Orthopaedics (SICOT), vol. 17, pp. 310-312, 1993.

KyphX Express System, Reducing the Profile. Increasing your Options. 6 pages.

KyphX® Bone Filler Device, web page at http://www1.kyphon.com/professionals/prod_KyphX_BFD.cfm, as available via the Internet and printed Jul. 6, 2005.

Orthopedic Devices; Classification for the Resorbable Calcium Salt Bone Void Filler Device, Food and Drug Administration, Rules and Regulations, Federal Register, vol. 68, No. 105, 2003.

Liu et al., Treatment Planning and Verification of HDR Brachytherapy Using C-arm Fluoroscopy, Department of Radiation Oncology, SUNY Upstate Medical University, Syracuse, New York.

METRx X™-Tube Retraction System-Innovative Design, web page at http://www.spineuniverse.com/displayarticle.php/article2146.html as printed on Jul. 5, 2005.

METRx™ System: Introduction, web page at http://www.spineuniverse.com/displayarticle.php/article748.html as printed on Jul. 5, 2005.

METRx™ Mimimal Access . . . : patient Info-SofamorDanek.com, web page at http://www.sofamordanek.com/patient-minimal-metrx.html as printed on Nov. 21, 2005.

* cited by examiner

SURGICAL ACCESS DEVICE, SYSTEM, AND METHODS OF USE

CROSS-REFERENCE TO RELATED APPLICATIONS

This application claims benefit of co-pending U.S. Provisional Patent App. No. 60/698,430, filed on Jul. 11, 2005, which is incorporated by reference herein in its entirety.

FIELD OF THE INVENTION

The present invention relates to a surgical access device, systems and kits comprising a surgical access device, and methods for making and using a surgical access device. Embodiments of the present invention are useful for performing minimally invasive surgery.

BACKGROUND OF THE INVENTION

Conventional surgical procedures for pathologies and/or trauma located deep within the body can cause significant trauma to intervening tissues. Open surgical procedures often require a long incision, extensive muscle stripping, prolonged retraction of tissues, denervation, and devascularization of tissue. Most of these surgeries require several hours of recovery room time and several weeks of post-operative recovery time due to the use of general anesthesia and the destruction of tissue during the surgical procedure. In some cases, these invasive procedures lead to permanent scarring and pain.

Minimally invasive alternatives, such as arthroscopic techniques, reduce pain, post-operative recovery time, and the destruction of healthy tissue. In minimally invasive surgery, the site of pathology is accessed through portals rather than through a significant incision, thus preserving the integrity of intervening tissues. These minimally invasive techniques also often require only local anesthesia. The avoidance of general anesthesia reduces post-operative recovery time and the risk of complications.

Minimally invasive surgical techniques are particularly desirable for spinal and neurosurgical applications because of the need for access to locations deep within the body and the danger of damage to vital intervening tissues. For example, a common open procedure for disc herniation, laminectomy followed by discectomy, requires stripping or dissection of the major muscles of the back to expose the spine. In a posterior approach, tissue including spinal nerves and blood vessels around the dural sac, ligaments, and muscle must be retracted to clear a pathway from the skin to the disc. These procedures normally take at least one to two hours to perform under general anesthesia and require post-operative recovery periods of at least several weeks. In addition to the long recovery time, the destruction of tissue is a major disadvantage of open spinal procedures. As a result, many patients may be reluctant to seek surgery as a solution to pain caused by spinal conditions.

In order to reduce the post-operative recovery time and pain associated with spinal and other procedures, micro-surgical techniques have been developed. For example, in micro-surgical discectomies, the disc can be accessed by cutting a pathway from the surface of the patient's back to the disc through a small incision. An operating microscope can be used to visualize the surgical field. Small diameter micro-surgical instruments may be passed through the small incision and between two laminae and into the disc. The intervening tissues are disrupted less because the incision and the exterior-to-interior pathway are smaller. Although these micro-surgical procedures are less invasive, they still involve some of the same risk of complications associated with open procedures, such as injury to the nerve root and dural sac, perineural scar formation, reherniation at the surgical site, and instability due to excess bone removal. A disadvantage of such micro-surgical techniques related to these types of complications is that they do not allow direct visualization of the surgical site by the surgeon.

The development of percutaneous spinal procedures has resulted in reduced recovery time and decreased post-operative pain because they require minimal, if any, muscle dissection and they can be performed under local anesthesia. For example, one such technique is a percutaneous lumbar discectomy using a lateral approach, preferably under fluoroscopic X-ray. Another percutaneous spinal procedure involves decompression of herniated discs with a posterolateral approach. This approach is a biportal procedure which involves percutaneously placing both a working cannula, by which fragments of the herniated disc are evacuated, and a visualization cannula for inserting an endoscope. This procedure allows simultaneous visualization and suction, irrigation, and resection in disc procedures. However, such conventional procedures are limited because they do not provide direct visualization of the surgical site and because they may require multiple entry portals into the patient. In addition, such lateral and postero-lateral approaches do not address spinal conditions which may require a mid-line approach or the removal of bone or implants.

Endoscopic surgical techniques allow a surgical procedure to be performed on a patient's body through a relatively small incision in the body and with a limited amount of body tissue disruption. Endoscopic surgery typically utilizes a tubular structure known as a cannula which is inserted into a small incision in the body. The cannula holds the incision open and serves as a conduit extending between the exterior of the body and the local area inside the body where the surgery is to be performed. Due to the relatively small size of the passage into the body defined by the cannula, certain surgical procedures, such as posterior discectomies and procedures using steerable surgical instruments, can be difficult to perform using endoscopic techniques.

One percutaneous approach to creating a surgical access passage utilizes a series of increasingly large dilation cannulae. In this technique, a small diameter cannula is inserted percutaneously to a surgical site. A slightly larger diameter cannula is then inserted around the smaller cannula in order to stretch the surrounding tissue. Increasingly larger cannulae, for example as many as a dozen cannulae, can be inserted one at a time, in order of increasing diameter, around the previously inserted cannula so as to incrementally retract surrounding tissue. This approach has the disadvantages of requiring use of a number of sterilized cannulae and traumatizing tissue each time a larger cannula is inserted.

Another approach to creating a surgical access passage, disclosed in U.S. Pat. No. 6,800,084 to Davison et al., involves a tubular cannula having a first tubular portion and a second tubular portion. The second tubular portion comprises an arcuate segment of cannula material rolled into tubular shape and attached to the distal end of the first tubular portion. After the cannula is percutaneously inserted to a surgical site, an expansion tool can be inserted through the cannula. A frustoconical tip of the expansion tool can be used to expand the distal portion of the cannula by unrolling the arcuate segment into a frustoconical shape.

The device and method disclosed by Davison et al. have several disadvantages. Although this approach provides an expanded work area at the surgical site (at the distal end of the cannula), it does not provide a larger, constant cross-sectional diameter along the entire length of the cannula so as to allow direct visualization of the entire operative site by the surgeon. Expansion of the second tubular portion of the cannula requires use of a separate expandable instrument that must be manipulated in numerous positions to fully expand the second tubular portion. The device and method disclosed by Davison et al. also have the disadvantage of lacking a mechanism for effectively maintaining the second tubular portion in its fully expanded position in a frustoconical shape. As a result, the surrounding tissue may begin to move back into the surgical field during a procedure and interfere with both visualization of the surgical site and the surgical procedure itself.

Surgical devices used in minimally invasive procedures often require provision of a light source to illuminate the surgical site. Conventional micro-surgical devices and endoscopic instruments often include a light source, for example, a fiber optic cable, integrated with or attached to the device or instrument. In percutaneous procedures, placing a light source such as a fiber optic cable through the surgical access passage can substantially obstruct the passage such that direct visualization of the surgical site is impeded.

Thus, there is a need for devices and methods that permit enlarged direct visualization of surgical procedures in a percutaneously-accessed surgical work space. There is a need for such devices and methods that provide access to and/or illumination at the surgical site without obstructing visualization of the site. There is a need for such devices and methods that reduce the number of portals into the patient. There is a need for devices and methods that provide for such percutaneous, minimally invasive surgery useful in a variety of applications and approaches.

SUMMARY OF THE INVENTION

The present invention provides a surgical access device, systems and kits comprising a surgical access device, and methods for manufacturing and using a surgical access device. Embodiments of the present invention are useful for creating and maintaining a surgical access passage for performing minimally invasive surgery in a human or animal.

In one embodiment, the present invention provides a surgical access device comprising an elongate member, which includes a proximal end, a distal end, and a plurality of retractor members. Each of the retractor members has an inner surface that together define a lumen of the elongate member. The elongate member lumen has a first cross-sectional dimension. Each of the plurality of retractor members can be moved radially outward to at least a second cross-sectional dimension. In one variation, the outward movement of the retractor members is configured to create a surgical access passage having a substantially constant cross-sectional dimension between the proximal end and the distal end of the elongate member from exterior the body to a surgical site. The resulting surgical access passage can receive instruments and allow direct access and/or visualization of the surgical site.

The surgical access device can include a mechanism and/or interface for moving the retractor members radially outward. The device can include a mechanism and/or interface for guiding the radially outward movement of the retractor members and a mechanism and/or interface for securing each of the retractor members in a range of positions. The device can further include a mechanism and/or interface for inserting the elongate member from exterior the body to the surgical site. The device can further include a mechanism and/or interface for illuminating the surgical site.

The present invention includes embodiments of a system comprising such a surgical access device for creating and maintaining a surgical access passage. The present invention includes embodiments of a kit comprising such a surgical access device. In some embodiments, a kit can comprise various combinations of elements. For example, a kit can include the elongate member, the mechanism for moving the retractor members radially outward, the mechanism for guiding the radially outward movement of the retractor members, the mechanism for securing each of the retractor members in a range of positions, the mechanism for inserting the elongate member from exterior the body to the surgical site, and/or the mechanism for illuminating the surgical site.

The present invention includes embodiments of methods for creating a surgical access passage in order to access a surgical site. Such an embodiment can utilize a surgical access device comprising an elongate member having a plurality of retractor members that can be moved radially outward from a first cross-sectional dimension to at least a second, larger cross-sectional dimension after the elongate member has been positioned in a patient. The method can further include steps for inserting the elongate member from exterior the body to the surgical site, guiding movement of the retractor members radially outward, securing each of the retractor members in a range of positions, and/or illuminating the surgical site.

Features of a surgical access device, systems, kits, and methods for making and using a surgical access device of the present invention may be accomplished singularly, or in combination, in one or more of the embodiments of the present invention. As will be realized by those of skill in the art, many different embodiments of a surgical access device, systems, kits, and methods for making and using a surgical access device according to the present invention are possible. Additional uses, advantages, and features of the invention are set forth in the illustrative embodiments discussed in the detailed description herein and will become more apparent to those skilled in the art upon examination of the following.

DETAILED DESCRIPTION

Figure 1:
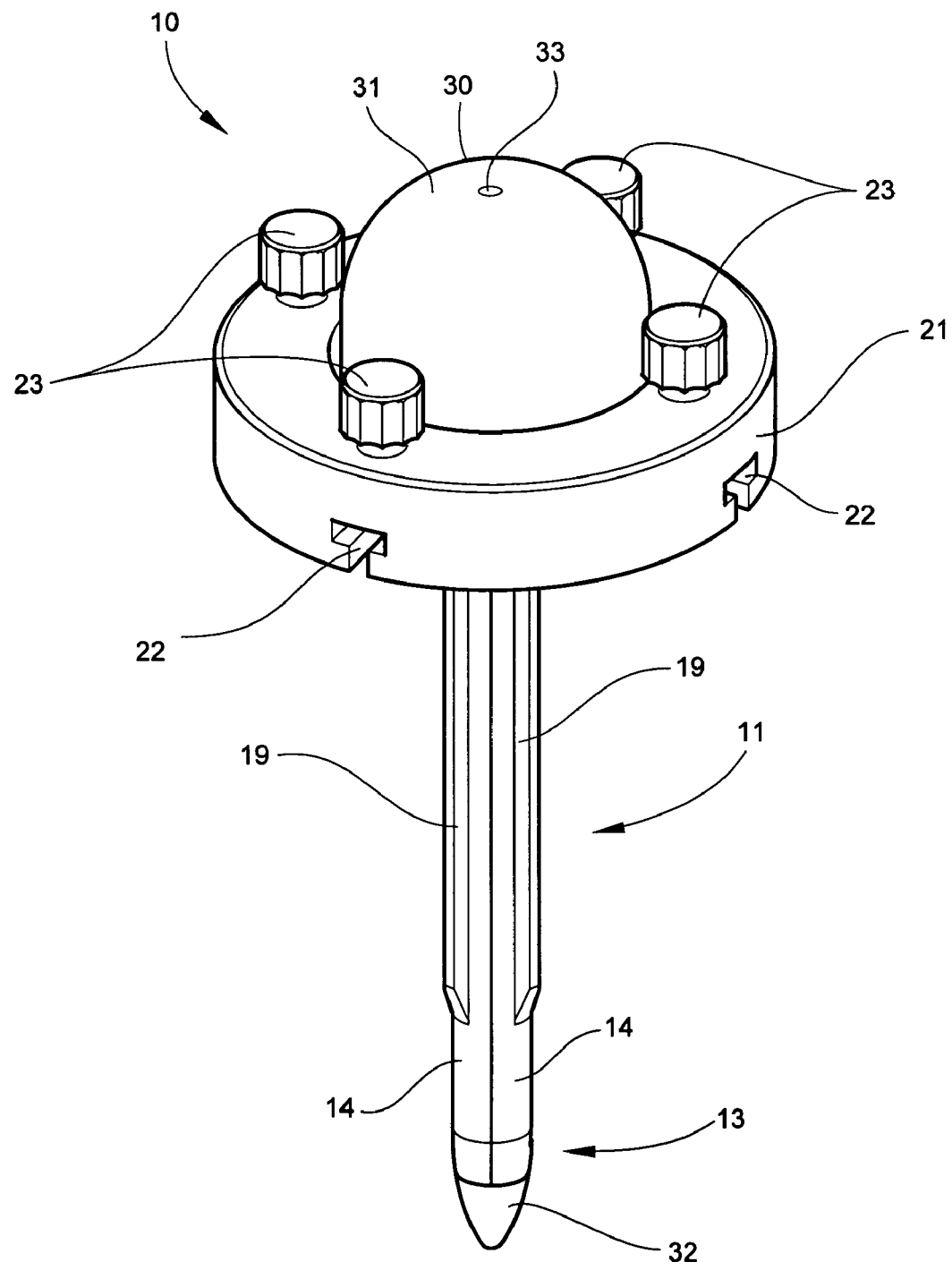
FIG. 1 is a perspective view of one variation of a surgical access device showing a retainer ring, four retractor members, four wheel locks, and a stylet inserted in the lumen of the surgical access device, in an embodiment of the present invention.

The present invention includes embodiments of a surgical access device, systems and kits comprising a surgical access device, methods of making a surgical access device, and methods of using a surgical access device. Embodiments of the present invention are useful for performing minimally invasive surgery.

As used in this specification and the appended claims, the singular forms "a," "an," and "the" include plural referents unless the context clearly dictates otherwise. Thus, for example, the term "a retractor member" is intended to mean a single retractor member or a combination of retractor members. As used in this specification and the appended claims, "proximal" is defined as nearer to a point of reference such as an origin, a point of attachment, or the midline of the body. As used in this specification and the appended claims, "distal" is defined as farther from a point of reference, such as an origin, a point of attachment, or the midline of the body. Thus, the words "proximal" and "distal" refer to direction nearer to and farther from, respectively, an operator (for example, surgeon, physician, nurse, technician, etc.) who inserts a medical device into a patient, with the tip-end (i.e., distal end) of the device inserted inside the patient's body. For example, the end of a medical device inserted inside the patient's body is the distal end of the medical device, while the end of the medical device outside the patient's body is the proximal end of the medical device.

In one embodiment, the present invention provides a surgical access device comprising an elongate member, for example, a cannula, comprising a mechanism for outward movement of the elongate member in situ (i.e., after the elongate member has been positioned in a patient). The mechanism for outward movement may comprise a plurality of rigid, inter-connected retractor members, each having an inner surface that together define a lumen of the elongate member. The retractor members may be moveable from a first cross-sectional dimension radially outward to at least a second, larger cross-sectional dimension. Such outward movement of the retractor members can create a surgical access passage having a substantially constant cross-sectional dimension between the proximal end and the distal end of the elongate member from exterior the body to a surgical site. The resulting surgical access passage may be capable of receiving instruments and allowing direct access and/or visualization of the surgical site.

The mechanism for outward movement of the elongate member may further comprise a retainer ring that can be positioned at the proximal end of the elongate member near the exterior of the body, and that is concentric to the elongate member. In an embodiment, the retainer ring functions to inter-connect the retractor members by positioning them such that they are spaced concentrically about the cannula. The retainer ring may further comprise guide channels into which retractor arms connected to the retractor members may be inserted. In this way, outward movement of the retractor members may be guided at least in part by movement of the retractor member arms through the guide channels.

The retainer ring may additionally comprise a mechanism for securing each of the retractor members in position both in their first position comprising a first cross-sectional dimension and in at least a second position corresponding to a second, larger cross-sectional dimension. In an embodiment, each of the retractor arms can be fixed in a specific position in one of the retainer member guide channels. For example, a screw or other type of adjustable device may be used to prevent the retractor arms from moving in the guide channels once the arms have been positioned at a desired location. In an embodiment, the mechanism to lock the retractor arms in place may comprise a plurality of wheel locks juxtaposed to the retractor arms and threadably adjustable through the retainer ring to engage the retractor arms.

A surgical access device of the present invention may further comprise positioning elements for positioning the device at the site requiring treatment. For example, the device may comprise a stylet for percutaneously inserting the elongate member, in which the retractor members are in a first, closed position, to a surgical site. The stylet may include a guide wire bore for positioning the stylet over a guide wire.

A surgical access device of the present invention may further comprise a mechanism for moving the retractor members radially outward. The mechanism for moving the retractor members radially outward may be used to urge the retractors from a first, closed position to at least a second, open position. The mechanism for moving the retractor members may comprise a first, unexpanded cross-sectional dimension that is less than the first, closed cross-sectional dimension of the elongate member, and at least a second, open cross-sectional dimension that is substantially the same as the second, open cross-sectional dimension of the elongate member. In an embodiment, the mechanism for moving the retractor members may comprise a balloon catheter or other inflatable member. Alternatively, other expandable devices may be used.

A surgical access device of the present invention may further comprise a mechanism and/or interface for illuminating the surgical site, such as a light source. In an embodiment, the mechanism for illuminating the surgical site may be positioned exterior of the elongate member. For example, the mechanism for illuminating the surgical site can be configured for operation at the distal end of a separate cannula. The separate cannula may comprise a mechanism for accessing the patient's interior. In such an embodiment, the separate cannula may be capable of guided percutaneous insertion through a second puncture pathway to the surgical site for positioning the light source at the periphery of the surgical site.

In an alternative embodiment, the mechanism and/or interface for illuminating the surgical site, or light source, may be positioned within the interior of the elongate member. For example, the mechanism for illuminating the surgical site can be provided at the distal end of the retractor members or along the length of the retractor members. In another embodiment, the mechanism for illuminating the surgical site can be provided in, or attached to, the inner (distal) face of the retainer ring so as to be directed toward the surgical site. In another embodiment, the surgical access device may further comprise a stabilization mechanism positionable inside the retractor members when they are in a position comprising the second cross-sectional dimension. In such an embodiment, the mechanism for illuminating the surgical site can be provided in or on the stabilization mechanism. In embodiments of the present invention comprising a mechanism for illuminating the surgical site, the surgical access passage is free from obstruction by the mechanism for illuminating the surgical site.

Referring now to the figures, in the embodiment shown in FIGS. 1-7, the surgical access device 10 may comprise an elongate member 11 having a proximal end 12 and a distal end 13. The elongate member 11 may have a plurality of retractor members 14, each having an inner surface 15 that together in closed position define a lumen 16 of the elongate member 11. The elongate member lumen 16 has a first cross-sectional dimension 17. Each of the retractor members 14 are moveable radially outwardly from a closed position having the first cross-sectional dimension 17 to an open position having at least a second, larger cross-sectional dimension 18. Such outward movement of the retractor members 14 can create a surgical access passage having a substantially constant cross-sectional dimension between the proximal end 12 and the distal end 13 of the elongate member 11 from exterior the body to a surgical site. The resulting surgical access passage is capable of receiving instruments and allowing direct access and/or visualization of a targeted surgical site.

In an embodiment, the elongate member 11 can include a plurality of retractor members 14, for example, four retractor members 14, as shown in FIGS. 1-7. The number of retractor members 14 can range from 2 to 20, or from 2 to 12, or from 2 to 6, or from 2 to 4. A support spine 19 may extend at least partly along the length of each retractor member 14, for example, on the exterior of the retractor members 14. The outer support spine 19 can provide additional rigidity to the retractor member 14 and help to provide support for the elongate member 11 as the retractor members 14 are moved outwardly and maintained in a position corresponding to the larger cross-sectional dimension 18.

The retractor members 14 are preferably sufficiently rigid to retract surrounding tissue when moved radially outward and to maintain that tissue in retracted position during a surgical procedure. The retractor members 14 can each have a blunt, or slightly rounded, distal end 13 to minimize trauma to tissue during insertion. Likewise, the distal end of each of the outer support spines 19 can be blunt or angled slightly inward so as to facilitate insertion through tissue. One or more of the retractor members 14 may comprise a hollow region for transferring material to and from the surgical site.

Each retractor member 14 can be moved radially outward to the open position having at least the second cross-sectional dimension 18 and can be moved radially inward back to the closed position having the first cross-sectional dimension 17. In an embodiment, each retractor member 14 can be moved independently of the other retractor members 14. Each of the retractor members 14, for example, each of the four retractor members 14 shown in the embodiment in FIGS. 1-7, can be moved radially outward to create at least the second cross-sectional dimension 18. In an embodiment, each of the retractor members 14 can be moved simultaneously.

Each retractor member 14 may further comprise a retractor member arm 20 extending outwardly at a substantially 90 degree angle from its proximal end 12 so as to be perpendicular to the longitudinal axis of the elongate member 11. The retractor member arm 20 can be integral with, or otherwise attached to, the retractor member 14. As shown in FIGS. 7-10, the retractor member arm 20 can be integral with the outer support spine 19 of the retractor member 14.

A retainer ring 21 can be configured for placement at the proximal end 12 of and concentric to the plurality of retractor members 14. The retainer ring 21 can be configured and/or adapted to rest on a patient's skin above a targeted surgical site. The retainer ring 21 can include a plurality of retractor member guide channels 22, in each of which a retractor member arm 20 can be positioned. The retractor member arms 20 may be slidable within the guide channels 22.

The surgical access device 10 can include a mechanism for securing the attached retractor member arms 20 and the retractor members 14 in a first position comprising the first cross-sectional dimension 17 and in at least a second position comprising the second cross-sectional dimension 18. For example, the mechanism for securing the retractor members 14 in position can be a wheel lock 23 threaded through a wheel lock guide 24 in the retainer ring 21 into each retainer member guide channel 22. The wheel lock 23 can be positioned into adjustable contact with the retractor member arm 20 in that guide channel 22. For example, the wheel lock 23 can be rotated downwardly to exert a movement-restricting force on the retractor member arm 20 and secure it into a desired position. Likewise, the wheel lock 23 can be rotated upwardly to release the movement-restricting force on the retractor member arm 20 so that the retractor member arm 20 can slide within the guide channel 22.

As shown in FIG. 1, the surgical access device 10 may include elements for positioning the device 10 at the site requiring treatment. For example, the device 10 may comprise a stylet 30 for percutaneously inserting the elongate member 11 to a surgical site. The stylet 30 may include a handle 31 for manipulating the stylet 30, a pointed tip 32, and a guide wire bore 33 extending through the length of the stylet 30. The stylet 30 can be inserted into the lumen 16 of the elongate member 11 when the retractor members 14 are in a first, closed position. In this manner, the guide wire bore 33 of the stylet 30 can be guided over a guide wire (not shown) for positioning the elongate member 11 at the surgical site.

Figure 2:
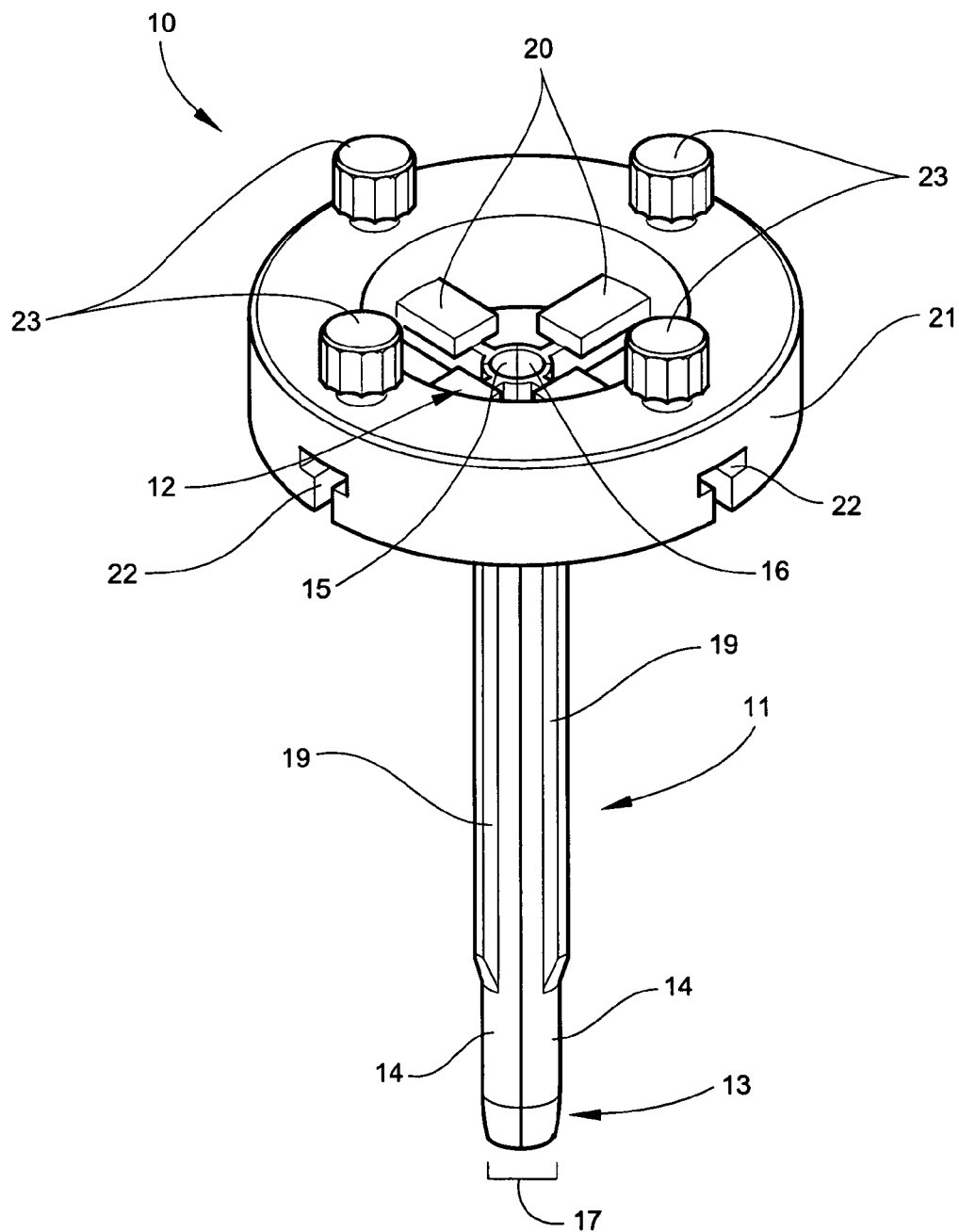
FIG. 2 is a perspective view of the surgical access device shown in FIG. 1, without the stylet, for example, after the device has been placed in position to create a surgical access passage, in an embodiment of the present invention.

The surgical access device 10 may be percutaneously inserted to a targeted surgical site using a variety of techniques. In one illustrative embodiment, a stab wound or small incision can be made in a patient's skin above a targeted surgical site. A small insertion cannula (not shown) having a sharp tip, for example, a trocar cannula, can be used to penetrate tissue to the surgical site. A guide wire (not shown) may be inserted through the insertion cannula. The insertion cannula can be removed, leaving the guide wire in place. With the stylet 30 inserted in the lumen 16 of the elongate member 11, the stylet 30 and elongate member 11 can then be threaded over the guide wire through the central guide wire bore 33 in the stylet 30. The guide wire has a diameter and rigidity sufficient to guide the elongate member 11 accurately to the surgical site. When the elongate member 11 is in a desired position, the guide wire and stylet 30 can be removed from the elongate member 11. FIG. 2 shows the surgical access device 10 after the stylet 30 has been removed, for example, after the elongate member 11 has been placed in position to create a surgical access passage to the surgical site.

In another embodiment, the insertion cannula utilized to create an initial percutaneous route to the surgical site can be a Jamshidi needle (not shown). The stylet 30 and elongate member 11 can be threaded over the Jamshidi needle to the surgical site. When the elongate member 11 is in a desired position, the Jamshidi needle and stylet 30 can be removed from the elongate member 11. Alternatively, the insertion cannula and guide wire, Jamshidi needle, or other insertion mechanism can be placed in the lumen 16 of the stylet 30 and/or elongate member 11 and inserted together with the stylet 30 and/or elongate member 11 to the surgical site.

Preferably, the retractor members 14 are inserted percutaneously to a surgical site in a collapsed, or closed, position such that the edges of the retractor members 14 are adjacent to each other. In this closed position, the retractor members 14 have an inner surface 15 that together define the lumen 16 of the elongate member 11. This closed lumen 16 of the elongate member 11 comprises the first cross-sectional dimension 17. When the elongate member 11 has been percutaneously inserted and positioned at a desired position adjacent a surgical site, the retainer ring 21 may be placed in a resting position on the patient's skin encircling the surgical access passage formed thereby.

Figure 3:
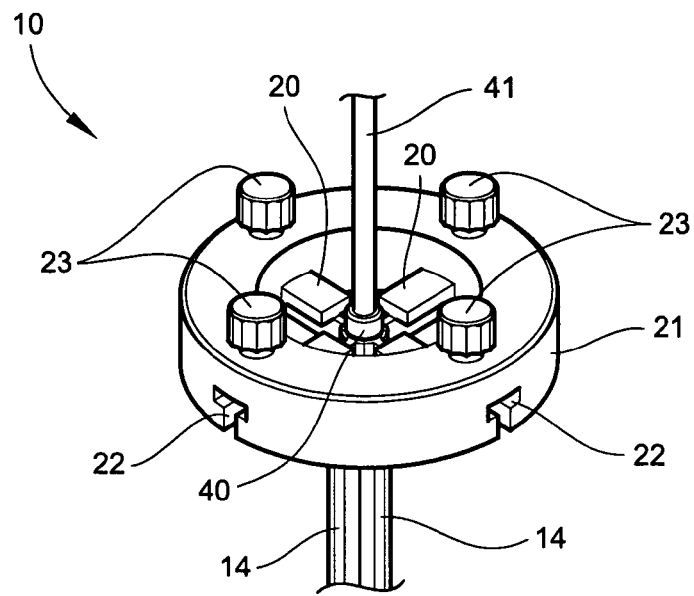
FIG. 3 is a perspective view of the surgical access device shown in FIG. 2, showing an expandable body, such as a balloon device, inserted into the surgical access device in unexpanded condition, in an embodiment of the present invention.

As shown in FIG. 3, the mechanism for moving the retractor members 14 radially outward can be an expandable body 40, such as a balloon. The expandable body 40 may be inserted into the lumen 16 of the elongate member 11 and can be actuated to apply a radially outward force to move the retractor members 14. The mechanism for moving the retractor members radially outward can be attached to the distal end of an elongate member 41, such as a small cannula or catheter. The expandable body 40 can be inserted in unexpanded condition into the lumen 16 of the elongate member 11. Once in position, the expandable body 40 can be expanded to cause the retractor members 14 of the elongate member 11 to move radially outwardly from their original closed position. Movement of the retractor members 14 radially outward causes surrounding tissue to be retracted, resulting in a surgical access passage inside the outwardly moved retractor members 14.

The surgical access passage created by such outwardly movement of the retractor members 14 can comprise a cross-sectional dimension from a range of cross-sectional dimensions between the first cross-sectional dimension 17 of the lumen 16 and a cross-sectional dimension equal to an inside diameter of the retainer ring 21. For example, the surgical access passage cross-sectional dimension may have a diameter in the range of ¾ inch to 1¼ inches. In embodiments, the surgical access passage cross-sectional dimension may have a diameter less than ¾ inch or greater than 1¼ inches, as the surgical approach may dictate or as the surgical procedure may require.

The expandable body 40, such as a balloon, can have a length that approximates the length of the retractor members 14 of the elongate member 11. As an example, in an embodiment of the present invention useful for spinal surgical procedures, the length of the elongate member 11 may be in the range of three to four inches. Thus, the expandable body 40 can be three to four inches in length. In an embodiment, the length of the expandable body 40 can be less than the length of the retractor members 14. For example, the expandable body 40 may comprise a length approximately one-third the length of the retractor members 14. The expandable body 40 having a length less than the length of the retractor members 14 can be inserted into the lumen 16 of the elongate member 11 such that it is adjacent, for example, the distal one-third of the retractor members 14. In this configuration, when the expandable body 40 is expanded, only the distal third of the retractor members 14 may be moved radially outward such that the distal portion of the surgical access passage is cone shaped.

Figure 4:
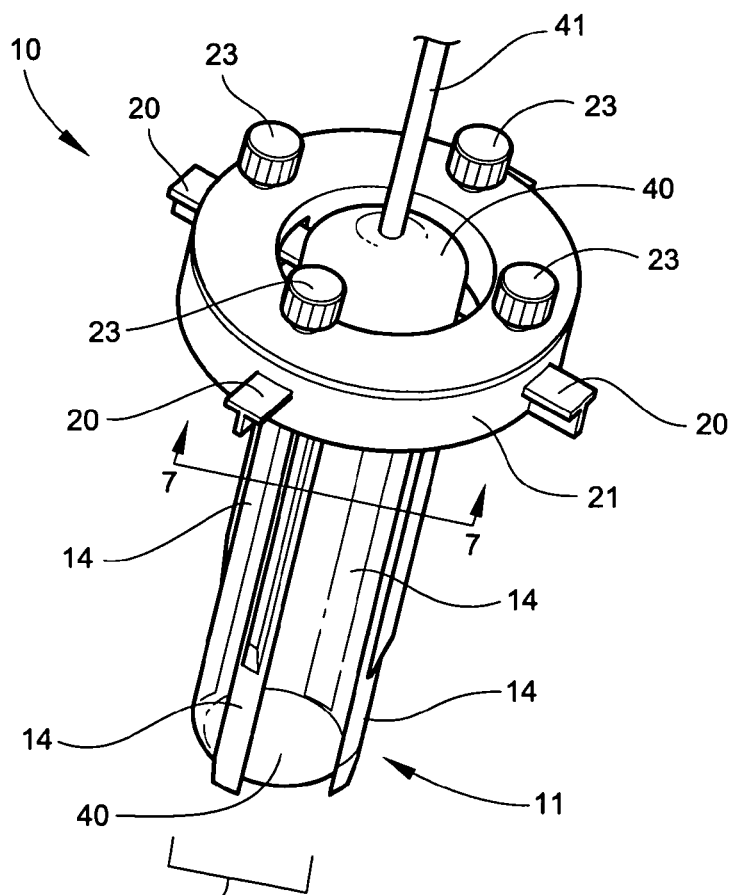
FIG. 4 is a perspective view of the surgical access device shown in FIG. 3, in which the expandable body is expanded, resulting in the radially outward expansion of each of the retractor members of the surgical access device, in an embodiment of the present invention.

As shown in the embodiment in FIG. 4, the mechanism for moving the retractor members 14 radially outward, such as the expandable body 40, can be expanded, or moved outwardly, inside the retractor members 14, resulting in outward movement of one or more of the retractor members 14 and thus retraction of adjacent surrounding tissue. When the expandable body 40 and retractor members 14 are moved outward to a desired at least second cross-sectional dimension 18, the wheel locks 23 on the top of the retainer ring 21 can be rotated downwardly to contact the retractor member arms 20 and lock the arms 20 and retractor members 14 in position.

Figure 5:
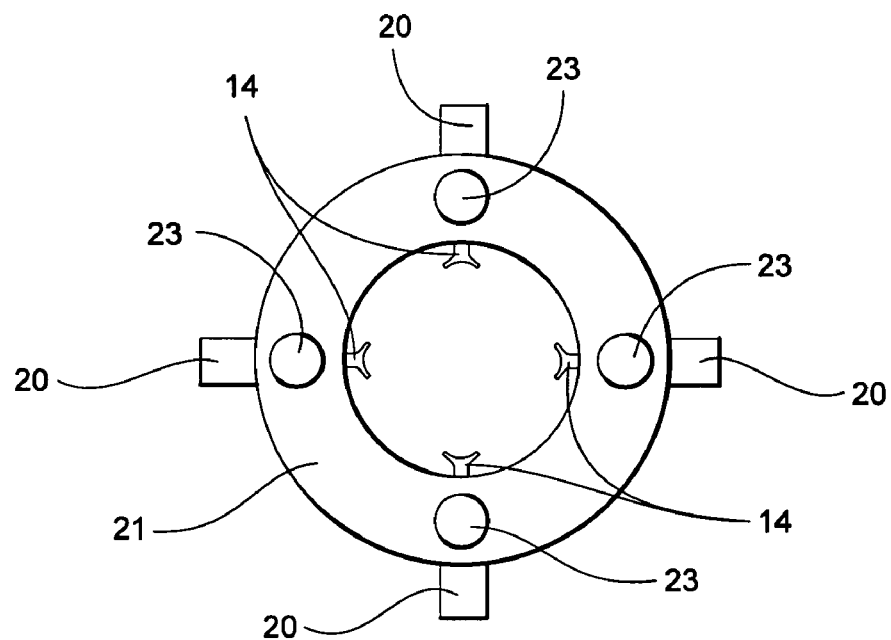
FIG. 5 is a top plan view of the surgical access device shown in FIGS. 1-4, after the retractor members have been expanded and the expandable body has been contracted and removed in an embodiment of the present invention.

FIG. 5 shows the surgical access device 10 after the retractor members 14 have been moved radially outward and the expandable body 40 has been contracted and removed from the elongate member 11. In this position, the retractor members 14 can provide a surgical access passage that allows the surgeon to directly visualize the surgical treatment site. As a result, the surgeon can directly visualize the anatomy and any trauma and/or pathology of a surgical site adjacent the surgical access passage, for example, an intervertebral disc. During performance of a surgical procedure, such as a laminectomy or discectomy, the surgeon can directly visualize and more accurately monitor movement of surgical instruments and manipulate tissue at the surgical site.

Figure 6:
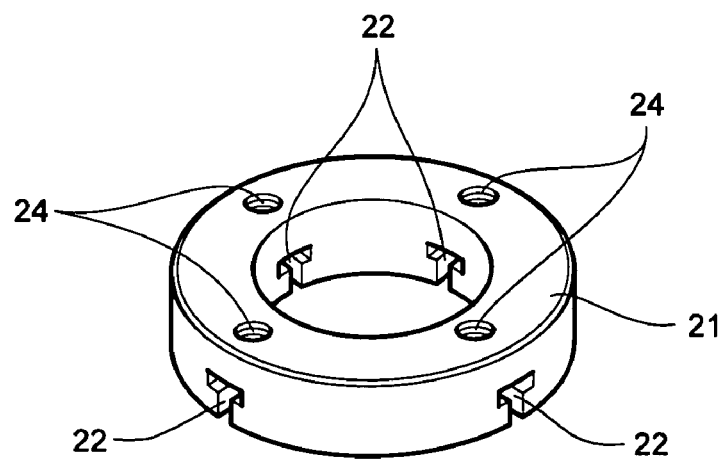
FIG. 6 is a perspective view of the retainer ring shown in FIG. 1, in which the retractor members, retractor member arms, and wheel locks have been removed in an embodiment of the present invention.
Figure 7:
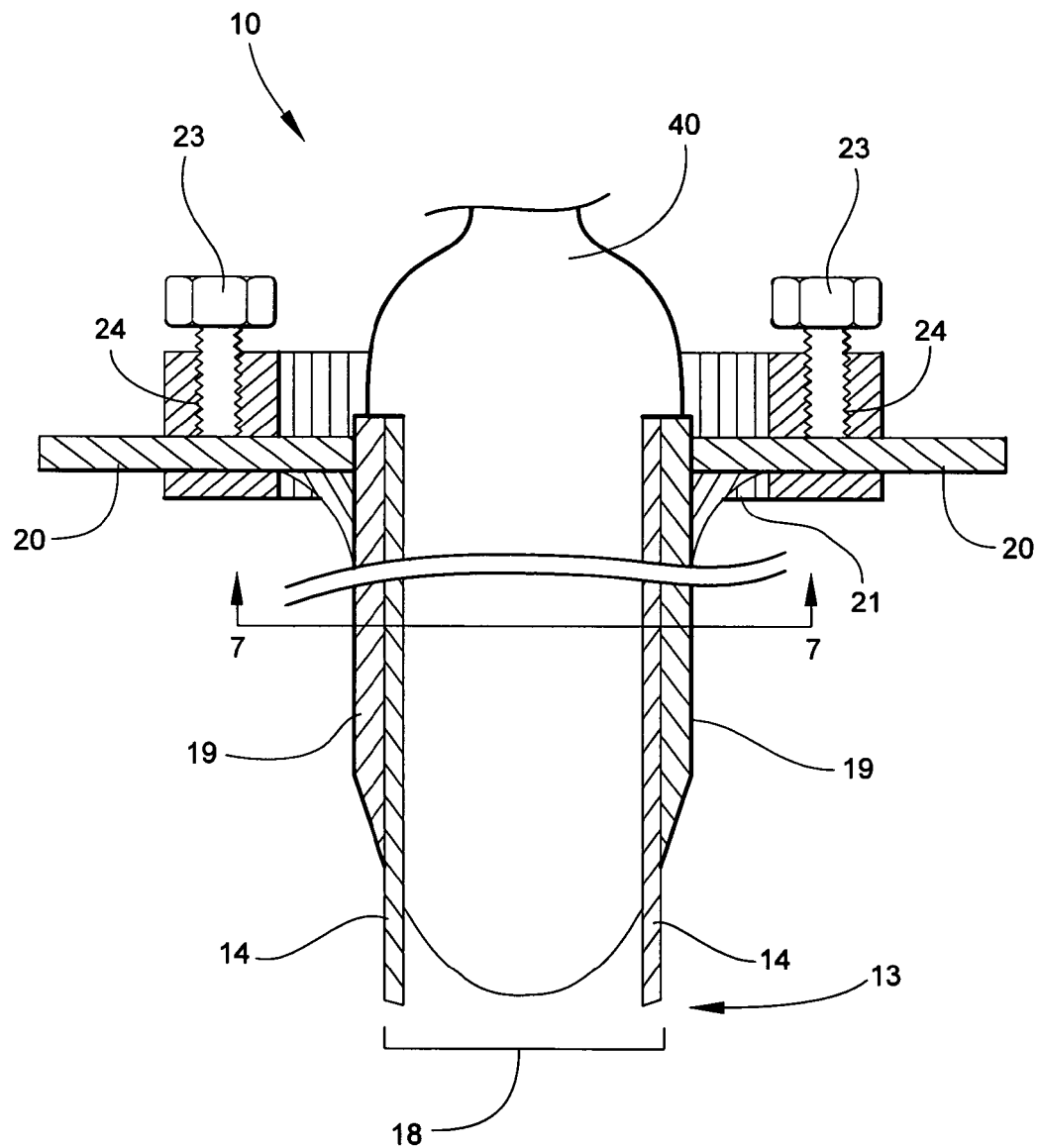
FIG. 7 is a diagrammatic, cross-sectional view of the surgical access device shown in FIG. 4, showing the expandable body in expanded position, the retractor members moved radially outward, and the wheel locks securing the retractor member arms and retractor members in a moved position in an embodiment of the present invention.

FIG. 6 shows the retainer ring 21 of FIG. 1, in which the elongate member 11, retractor members 14, and wheel locks 23 have been removed. Each retractor member arm 20 can slide along the axis of a T-shaped retractor member guide channel 22 so as to allow the retractor members 14 to move radially outward and inward. FIG. 7 is a cross-sectional side view of the surgical access device 10 shown in FIG. 4, showing the expandable body 40 in expanded position and retractor members 14 moved radially outward. The wheel locks 23 can be inserted into the matingly threaded wheel lock guides 24, or screw holes, located directly above the retractor member guide channels 22. When the retractor member 14 is in a desired position, the wheel lock 23 can be rotated downwardly to contact the retractor member arm 20 and secure it and the retractor member 14 in position, as shown in FIG. 7. Likewise, when it is desired to move the retractor members 14 to another position—either outwardly or inwardly—the wheel lock 23 can be rotated upwardly to release contact of the wheel lock 23 with the retractor member arm 20 so that the retractor member arm 20 can slide along the guide channel 22 to another position. Wheel locks 23 can be used to secure the retractor members 14 in a closed position for percutaneous insertion of the elongate member 11 to a surgical site.

In an embodiment, one or more retractor members 14 can be hollow, and can be used to remove material from, and/or insert materials into, the surgical site.

In some embodiments of the surgical access device 10, the retractor members 14 can be moved radially outward with a different mechanism and/or interface for that purpose. In addition to outward movement with an expandable body 40, or balloon, the retractor members 14 can be moved radially outwardly by a hydraulic mechanism, by mechanical actuation, or by other suitable mechanism.

Figure 19A:
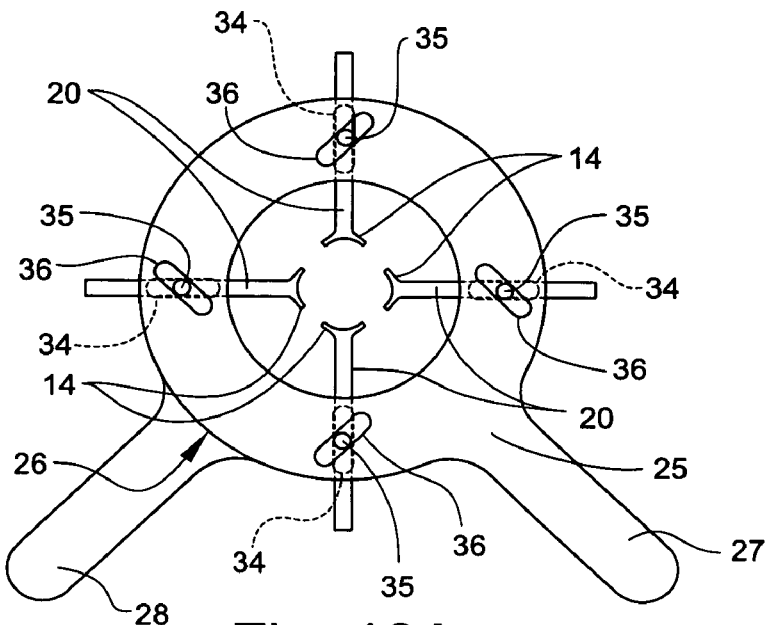
FIG. 19A is a top plan view of one variation of slidingly rotatable upper and lower retainer rings of a surgical access device in another embodiment of the present invention.
Figure 19B:
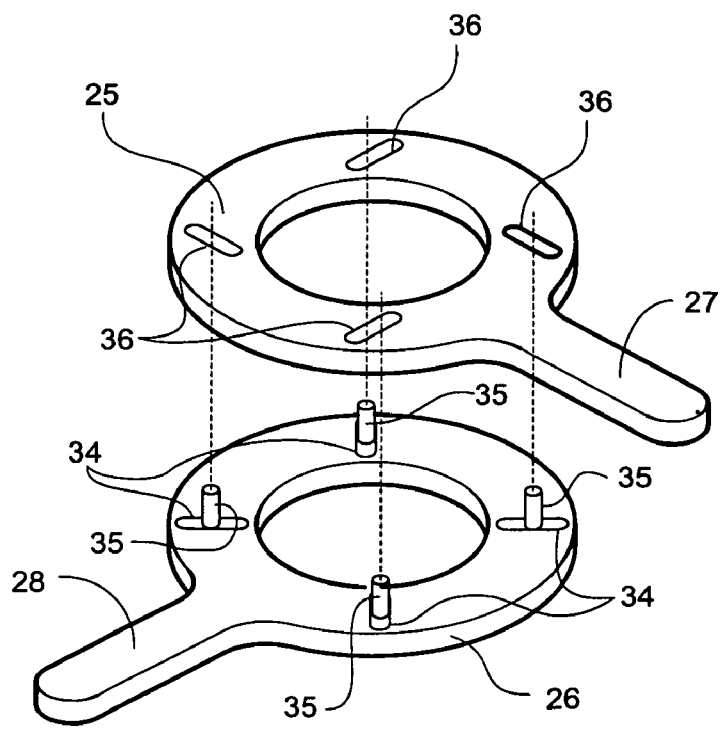
FIG. 19B is a perspective view of the upper and lower retainer rings shown in the embodiment in FIG. 19A, showing the retainer rings in disassembled arrangement.

For example, as shown in the embodiment in FIGS. 19A-19B, the surgical access device 10 can include two retainer rings, an upper retainer ring 25 and a lower retainer ring 26. The bottom surface of the upper retainer ring 25 rests on the top surface of the lower retainer ring 26. The upper and lower retainer rings 25, 26 are engageable with each other and slidingly rotatable relative to each other. The upper and lower retainer rings 25, 26, respectively, can be engaged with each other in various appropriate manners for rotating the retainer rings 25, 26 relative to one another. For example, the upper and lower retainer rings 25, 26, respectively, can include interlocking grooves in their interfacing surfaces to allow sliding rotation of the retainer rings 25, 26. Sliding rotation of the upper and lower retainer rings relative to one another can be accomplished by moving the upper retainer ring handle 27 and/or the lower retainer ring handle 28 toward or away from the other handle 27, 28.

The lower retainer ring 26 includes a retractor member guide channel 22 (not shown in FIGS. 19A-19B) for each retractor member arm 20, as shown in FIGS. 1-3 and 6. In the embodiment in FIGS. 19A-19B, the lower retainer ring 26 includes a lower retainer ring slot 34 (shown best in the disassembled view of the retainer rings 25, 26 in FIG. 19B) located above and parallel to the longitudinal axis of each guide channel 22. Each of the retractor member arms 20 includes a peg 35 that extends upward at a substantially 90 degree angle from the retractor member arm 20 through the lower retainer ring slot 34 located above that retractor member arm 20. Each of the retractor member arm pegs 35 is movable within the lower retainer ring slot 34 through which it extends. That is, as the retractor member arm 20 moves outwardly and inwardly through its respective guide channel 22, the retractor member arm peg 35 moves the same direction and distance as the retractor member arm 20 outwardly or inwardly in the lower retainer ring slot 34 above that guide channel 22.

The upper retainer ring 25 includes an upper retainer ring slot 36 located above each lower retainer ring slot 34. The center of each upper retainer ring slot 36 is located approximately above the center of the lower retainer ring slot 34 below it. Each of the retractor member arm pegs 35 extending through its respective lower retainer ring slot 34 extends upward through the upper retainer ring slot 36 located above that lower retainer ring slot 34. Each upper retainer ring slot 36 is angled relative to the orientation of the lower retainer ring slot 34 below it such that when the upper and lower retainer ring handles 27, 28, respectively, are moved relative to each other, the upper retainer ring slot 36 presses against the peg 35 extending through the slots 34, 36, causing the peg 35 to move outwardly or inwardly, depending on the direction of handle 27, 28 movement. In this manner the retractor member arms 20 and the retractor members 14 connected thereto can be moved a desired amount outwardly and/or inwardly. Movement of the retractor members 14 radially outward in this manner causes surrounding tissue to be retracted, resulting in a surgical access passage inside the outwardly moved retractor members 14 that allows direct access and visualization of the surgical site.

An embodiment of a surgical access device 10 having slidingly engageable upper and lower retainer rings 25, 26, respectively, can include a suitable mechanism for securing the retainer rings 25, 26 into a desired position. For example, the retainer rings 25, 26 can include a wheel lock (not shown in FIGS. 19A-19B) similar to the wheel lock 23 (as shown in FIGS. 1-4) that can be threaded through a wheel lock guide 24 in the upper retainer ring 25 into adjustable contact with the lower retainer ring 26. The wheel lock 23 can be rotated downwardly to exert a movement-restricting force between the upper and lower retainer rings 25, 26, respectively, to secure the retainer rings 25, 26 into a desired position. Accordingly, the retainer rings 25, 26 can be secured so as to secure the retractor members 14 in a first position comprising the first cross-sectional dimension 17 and in at least a second position comprising the second cross-sectional dimension 18. Likewise, the wheel lock 23 can be rotated upwardly to release the movement-restricting force between the retainer rings 25, 26 so that the retainer rings 25, 26 can be moved relative to each other. Other suitable securing mechanisms can be utilized for securing the retainer rings 25, 26 into a desired position.

In the embodiment shown in FIGS. 19A-19B, the upper retainer ring slots 35 are angled at an approximately 45 degree angle relative to the lower retainer ring slots 34. In other embodiments, the upper retainer ring slots 36 can be angled in various degrees so as to cause the pegs 35 to be moved outwardly and/or inwardly when the upper and lower retainer ring handles 27, 28, respectively, are moved relative to each other.

In an alternative embodiment, the upper retainer ring 25 may be removable from the lower retainer ring 26. The embodiment shown in FIGS. 19A-19B includes an upper retainer ring slot 36 for each retractor member arm 20. In an embodiment (not shown) in which the upper retainer ring 25 is removable from the lower retainer ring 26, the upper retainer ring 25 may include fewer slots 36 than the number of retractor member arms 20. For example, if it is desired to move only one retractor member 14 at a time, the upper retainer ring 25 may comprise only one slot 36. In this way, once a first retractor member 14 has been moved to a desired position (either outwardly or inwardly) by moving the upper and lower retainer ring handles 27, 28, respectively, relative to each other, the upper retainer ring 25 can be removed from the lower retainer ring 26. The upper retainer ring 25 can be re-engaged with the lower retainer ring 26 such that the upper retainer ring slot 36 aligns with a second lower retainer ring slot 34 and peg 35. Then, the handles 27, 28 can be moved relative to each other to move the second retractor member 14 to a desired position. These steps can be repeated to move other retractor members 14 as desired. Moving retractor members 14 independently of one another allows creation of a surgical access passage having various configurations.

Figure 20A:
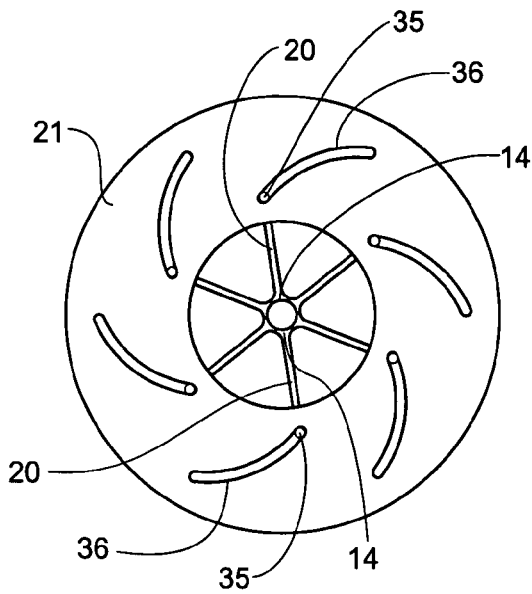
FIG. 20A is a top plan view of another variation of a retainer ring showing retractor members in closed position in an embodiment of the present invention. The pegs attached to retractor member arms are shown in a closed position adjacent the inner aspect of the retainer ring slots.
Figure 20B:
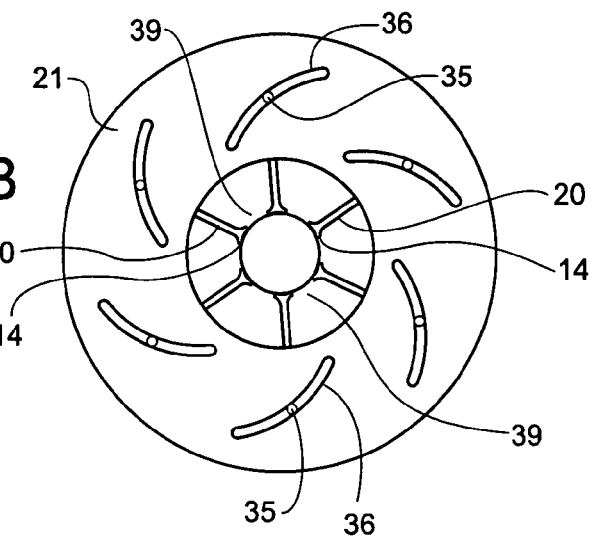
FIG. 20B is a top plan view of the retainer ring shown in FIG. 20A, showing retractor members in an intermediate open position and the pegs attached to retractor member arms near the center of the retainer ring slots.
Figure 20C:
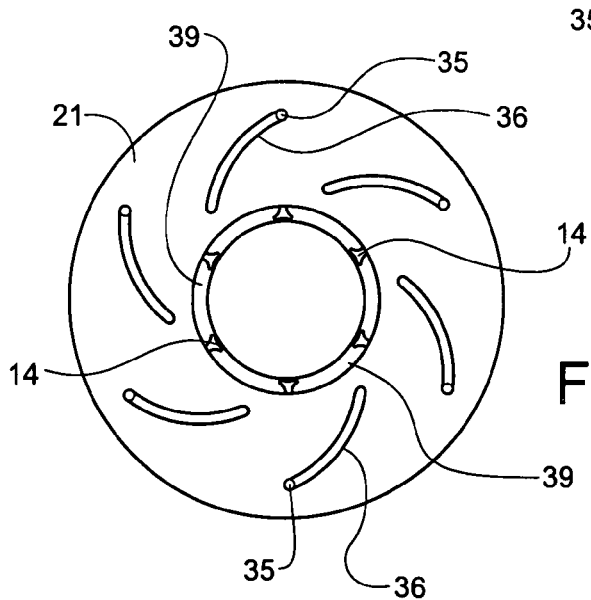
FIG. 20C is a top plan view of the retainer ring shown in FIGS. 20A and 20B, showing retractor members in a fully open position and the pegs attached to retractor member arms adjacent the outer aspect of the retainer ring slots.

FIGS. 20A-20C show another embodiment of a mechanism for moving the retractor members 14 radially outward and inward in the surgical access device 10. In this variation of the surgical access device 10, the retainer ring 21 includes a retainer ring slot 36 positioned above each retractor member arm 14. The retainer ring 21 is rotatable relative to the retractor member guide channels 22 (as shown in FIGS. 1-4). For example, the retainer ring 21 can comprise two interfacing components, an upper component that includes the retainer ring slots 36 and a lower component in which the guide channels 22 are disposed. The upper and lower components (which can be similar to the upper and lower retainer rings 25, 26, respectively, as shown if FIGS. 19A-19B) can be engaged with each other in various appropriate manners for rotating the upper and lower components relative to one another. For example, the upper and lower components can include interlocking grooves in their interfacing surfaces to allow sliding rotation of the upper and lower components relative to each other. In such an embodiment, sliding rotation of the upper and lower retainer ring components relative to one another can be accomplished by rotating the upper component.

Each of the retractor member arms 20 includes a peg 35 that extends upward at a substantially 90 degree angle from the retractor member arm 20 through the retainer ring slot 36 located above that retractor member arm 20. Each of the retractor member arm pegs 35 is movable within the retainer ring slot 36 through which it extends. That is, as the retractor member arm 20 moves outwardly and inwardly through its respective guide channel 22, the retractor member arm peg 35 moves the same direction and distance as the retractor member arm 20 outwardly or inwardly in the retainer ring slot 36 above that guide channel 22.

Each retainer ring slot 36 is angled relative to the orientation of the guide channel 22 below it. In the embodiment shown in FIGS. 20A-20C, the retainer ring slots 36 comprise an arcuate shape, the center of each of which is positioned approximately above the center of the guide channel 22 below it. In this manner, when the retainer ring 21 is rotated, the retainer ring slot 36 presses against the peg 35 extending through the slot 36, causing the peg 35 to move outwardly or inwardly, depending on the direction of rotation. Accordingly, the retractor member arms 20 and the retractor members 14 connected thereto can be moved a desired amount outwardly and/or inwardly. Movement of the retractor members 14 radially outward in this manner causes surrounding tissue to be retracted, resulting in a surgical access passage inside the outwardly moved retractor members 14 that allows direct access and visualization of the surgical site.

Such an embodiment can include a suitable mechanism for securing the retractor members 14 into a desired position. For example, the retainer ring 21 can include a wheel lock (not shown in FIGS. 20A-20C) similar to the wheel lock 23 (as shown in FIGS. 1-4) that can be threaded through a wheel lock guide 24 through the retainer ring 21 into adjustable contact with the retractor member arm 20 below the wheel lock 23, as described with reference to FIGS. 1-4

The movement of the retainer ring slots 36 relative to the pegs 35 and the associated movement of the retractor member arms 20 and retractor members 14 is illustrated in the sequence of positions shown in FIGS. 20A-20C. The retractor members 14 are shown in a closed position in FIG. 20A, with the pegs 35 attached to retractor member arms 20 positioned adjacent the inner aspect of the retainer ring slots 36. From this closed position, the retainer ring 21 can be rotated relative to the guide channels 22, such that the retractor members 14 are moved to a first open position (as shown in FIG. 20B). In this first open position, the pegs 35 attached to retractor member arms 20 are positioned near the center of the retainer ring slots 36. The retainer ring 21 can be further rotated relative to the guide channels 22, such that the retractor members 14 are moved to a second open position (as shown in FIG. 20C), which in this case is a fully open position. When the retractor members 14 are in the fully opened position, the pegs 35 attached to retractor member arms 20 are positioned adjacent the outer aspect of the retainer ring slots 36. This type of rotating movement of the retainer ring 21 relative to the guide channels 22 and associated radial movement of the retractor members 14 illustrated in FIGS. 20A-20C is analogous to the rotational movement of an adjustment ring that can cover and uncover a camera lens. The retractor members 14 can be moved radially outward and inward to any number of positions between a fully closed position and a fully open position.

The number of retractor members 14, retractor member arms 20, and retainer ring slots 36 can vary. The embodiment in FIGS. 20A-20C includes six retractor members 14 and connected retractor member arms 20, and six retainer ring slots 36 (one slot 36 for each retractor member arm 20). (For convenience, only two each of the retractor members 14, retractor member arms 20, and retainer ring slots 36 are labeled in FIGS. 20A-20C.)

In an embodiment of the present invention, the surgical access device 10 may include a material 39, for example, as shown in FIGS. 20A-20C, attached to the retractor members 14 that provides a barrier between retracted tissue and the surgical access passage created by outward movement of the retractor members 14. In an embodiment, the material 39 can be a solid tubular material, for example, a thin polymeric elastic material such as latex, placed about the exterior of the retractor members 14 in closed position, as shown in FIG. 20A. The material 39 can be attached to the exterior of the retractor members 14, for example, by sealing the material 39 to the retractor members 14 with radio frequency or laser sealing or by other suitable mechanisms.

In an alternative embodiment, the material 39 can be sheet material, such as sheets of a thin polymeric elastic material, attached to adjacent retractor members 14. The barrier material 39 can be attached between at least two of the retractor members 14. Alternatively, the barrier material 39 can be attached between each pair of adjacent retractor members 14. When the retractor members 14 are moved outwardly, as shown in FIGS. 20B and 20C, to create a surgical access passage, the material 39 (either in tubular or sheet form) stretches outwardly to provide a barrier between retracted tissue and the surgical access passage. Such a barrier can help provide and maintain a clear passage to facilitate direct access and visualization of the surgical site.

Figure 21:
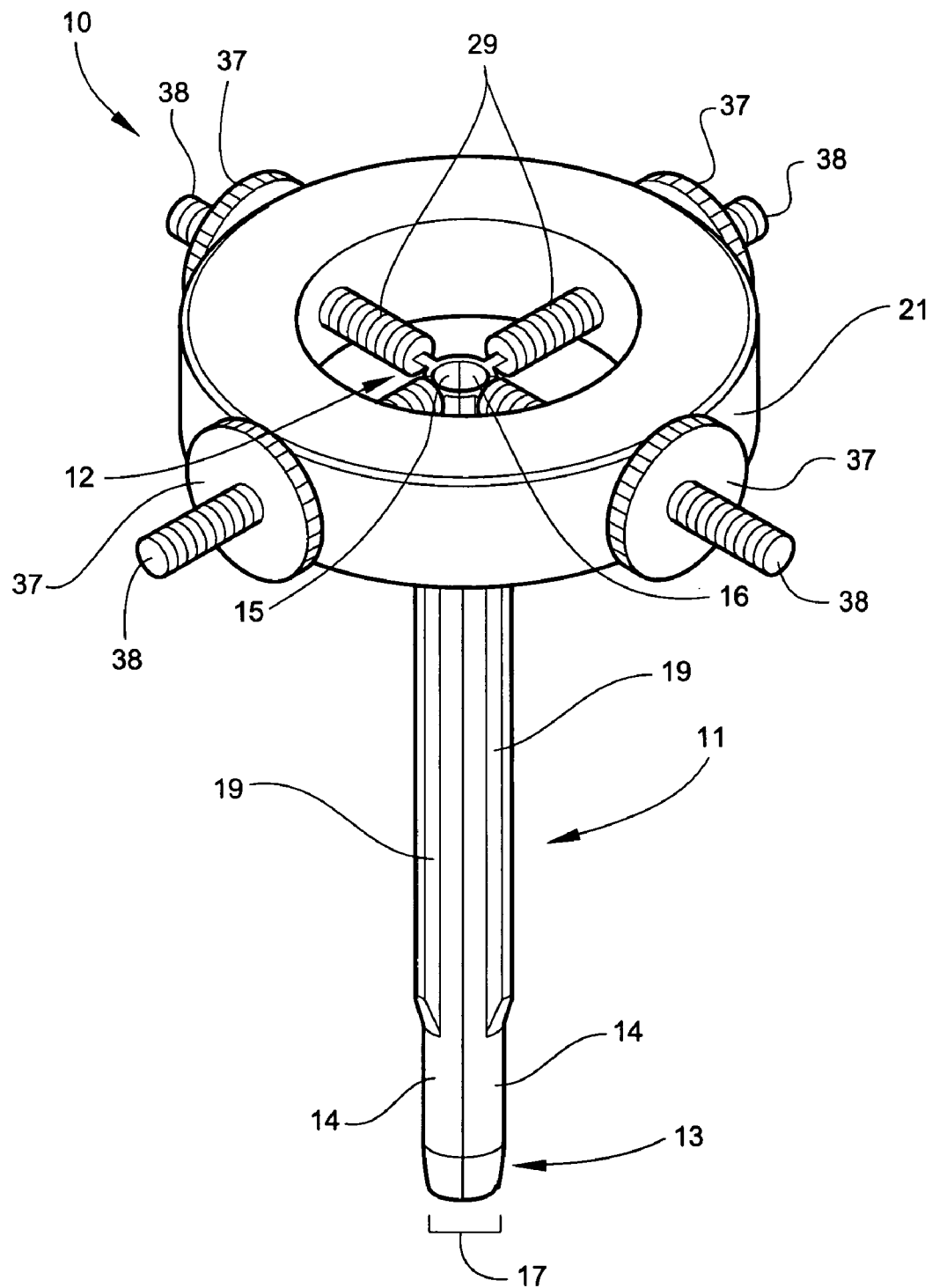
FIG. 21 is a perspective view of a surgical access device having threaded retractor member arms and rotation wheels in another embodiment of the present invention.

In another embodiment, the surgical access device 10 can include the mechanism for moving the retractor members 14 radially outward and inward illustrated in FIG. 21. In this embodiment, each of the retractor members 14 is connected to a threaded retractor member arm 29. The threaded retractor member arm 29 is connected to the retractor member 14 such that the threaded retractor member arm 29 can be rotated (such as about a rotatable pivot joint) at the connection point with the retractor member 14. That is, the threaded retractor member arm 29 can be rotated while the retractor member 14 does not rotate. Each threaded retractor member arm 29 is rotatingly threaded through a matingly threaded retractor member guide channel (not shown) similar to the retractor member guide channels 22 shown in FIGS. 1-3 and 6. Each threaded retractor member arm 29 may also be inserted through a rotation wheel 37 adjacent to the exterior of the retainer ring 21 such that an end 38 of the threaded retractor member arm 29 extends through the rotation wheel 37.

The rotation wheel 37 may be fixedly attached to the threaded retractor member arm 29 or rotatable about the threaded retractor member arm 29. In an embodiment in which the rotation wheel 37 is fixedly attached to the threaded retractor member arm 29, the mechanism for moving the retractor member 14 outwardly and inwardly can comprise the rotation wheel 37 and threaded retractor member arm 29. The rotation wheel 37 can be rotated to rotate the threaded retractor member arm 29 to move the arm 29 radially outward and/or inward through the threaded retractor member guide channel, causing the attached retractor member 14 to move radially outward and/or inward.

When the retractor member 14 is in a desired position, for example, at a position retracting tissue to help form the second cross-sectional dimension 18, the retractor member 14 can be secured in that position. The threaded retractor member arm 29 and attached retractor member 14 can be secured in a desired position by various suitable mechanisms. For example, the retainer ring 21 can include a wheel lock (not shown in FIG. 21) similar to the wheel lock 23 (as shown in FIGS. 1-4) that can be threaded through a wheel lock guide 24 in the retainer ring 21 into adjustable contact with the threaded retractor member arm 29. The wheel lock 23 can be rotated downwardly to exert a movement-restricting force against the threaded retractor member arm 29 to secure the threaded retractor member arm 29 and attached retractor member 14 into a desired position. Likewise, the wheel lock 23 can be rotated upwardly to release the movement-restricting force against the threaded retractor member arm 29 so that the threaded retractor member arm 29 and attached retractor member 14 can be moved to another position.

In an embodiment in which the rotation wheel 37 is rotatable about the threaded retractor member arm 29, the threaded retractor member arm 29 can be rotated to move the arm 29 outwardly through the threaded retractor member guide channel, causing the attached retractor member 14 to move outwardly. The rotation wheel 37 may then be rotated about the threaded retractor member arm 29 until the rotation wheel 37 rests against the exterior surface of the retainer ring 21. In this manner, the rotation wheel 37 can be utilized as a mechanism for securing the threaded retractor member arm 29 and the retractor member 14 in a desired position to maintain tissue retraction for creating direct access and visualization of a targeted surgical site.

In an embodiment in which each retractor member 14 has a threaded retractor member arm 29 rotatably connected to it, each retractor member 14 can be moved outwardly and inwardly independently of other retractor members 14. Such an embodiment thus provides the operative flexibility to allow retraction of tissue in an uneven fashion so as to create and maintain a surgical access passage having an asymmetrical cross-section. In one illustrative application, the surgical access device 10 can be inserted in a patient adjacent the spinus process of a vertebral body, where it may be desired to restrict movement of tissue toward the spinus process. The operator may move three of the retractor members 14 of the embodiment shown in FIG. 21 radially outward so as to retract tissue in those three directions, while leaving the retractor member 14 adjacent the spinus process in its original, inward position. In this way, a minimally invasive surgical access passage can be created immediately adjacent the spinus process without displacing tissue toward the spinus process.

Embodiments of a surgical access device 10 of the present invention can include a mechanism and/or interface for illuminating a surgical site. As shown in the embodiments in FIGS. 8-9, the mechanism for illuminating a surgical site can comprise a rotatable arm 50 rotatably mounted to the retainer ring 21 and a curved insertion member 51 attached to the rotatable arm 50. The rotatable arm 50 can be rotatably mounted to a pivot 52 in a rotatable arm support 53 on the retainer ring 21. The curved insertion member 51 can be a curved cannula having a sharp tip and attached to the distal end of the rotatable arm 50. A light source 60 can be attached or integrated at the distal tip of the curved insertion member 51. The light source 60 can be any suitable light source for illuminating a surgical site, including, for example, a fiber optic light source. In conventional surgical techniques, a surgical site may be illuminated by inserting a light source separate from a retraction device through the surgical access passage. In this approach, the light source may interfere with access and/or visualization of the surgical site during the procedure.

Figure 9:
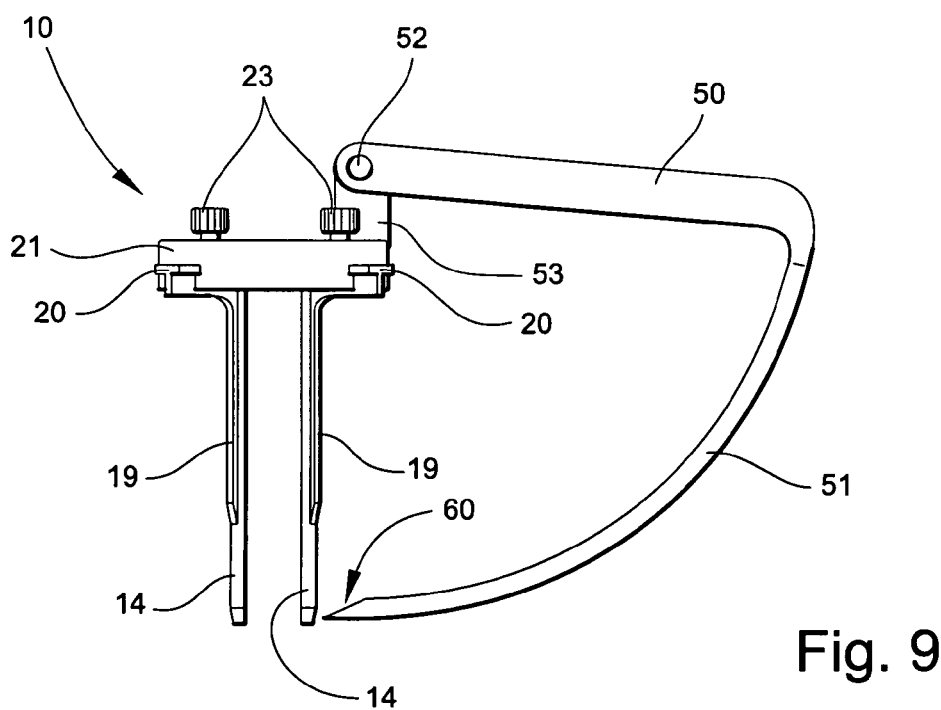
FIG. 9 is a side view of the surgical access device shown in FIG. 8, having the rotatable arm rotated downward such that the curved cannula would be inserted through the skin and subcutaneous tissue layers via a secondary puncture portal so that the tip of the curved cannula is positioned at the periphery of the surgical site, in an embodiment of the present invention.

As shown in the embodiment in FIG. 9, the rotatable arm 50 can be rotated downward such that the curved insertion cannula member 51 would be inserted through the skin and subcutaneous tissue layers via a secondary puncture pathway separate from the surgical access passage. In this manner, percutaneous insertion of the insertion member 51 allows the light source 60 at the distal tip of the curved insertion member 51 to be positioned at a desired location at a periphery of the surgical site. The length of the rotatable arm 50 and the length and curvature of the curved insertion cannula member 51 can be pre-determined so that when the curved insertion member 51 is inserted percutaneously and the rotatable arm 50 reaches a predetermined position, such as an approximately 90 degree angle with the longitudinal axis of the elongate member 11, the tip of the curved insertion member 51 is positioned precisely at the desired location at the periphery of the surgical site. The curved insertion member 51 can have a different length and curvature for an elongate member 11 having retractor members 14 of a different dimension so that when inserted, the tip of the curved insertion member 51 can be aligned with the surgical site. A light source 60 in the curved insertion member 51 can then provide illumination of the surgical site without interfering with the surgeon's access and/or visualization of the site.

Figure 10:
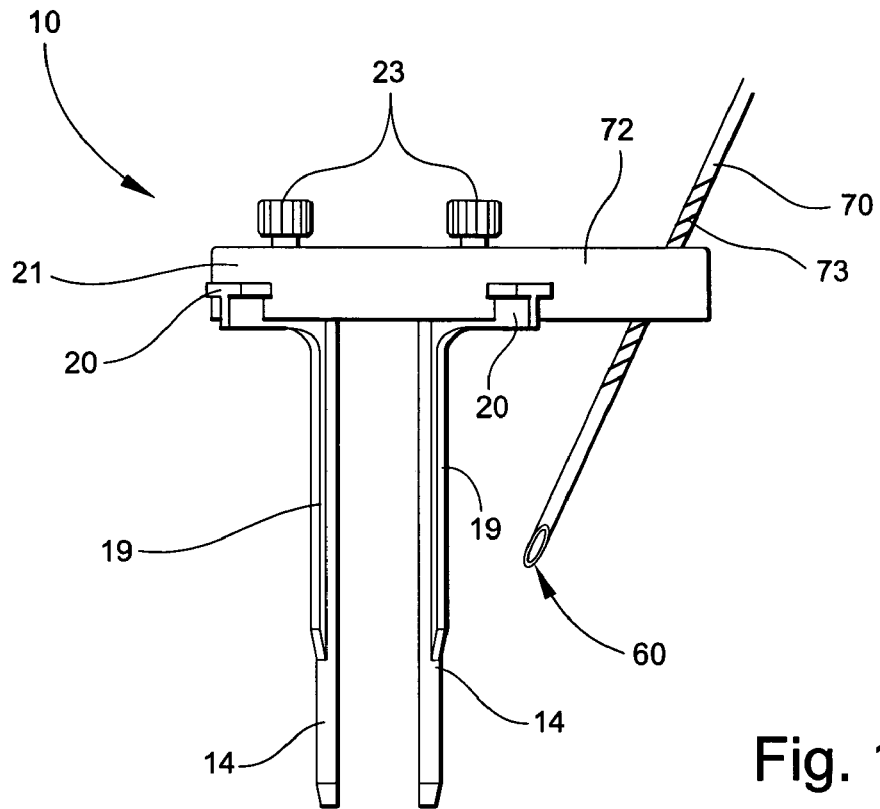
FIG. 10 is a side view of the surgical access device shown in FIGS. 1-4, the retainer ring having an arm extending outwardly and including a guide slot for receiving and guiding percutaneous insertion of a straight cannula having a light source, in an embodiment of the present invention.
Figure 11:
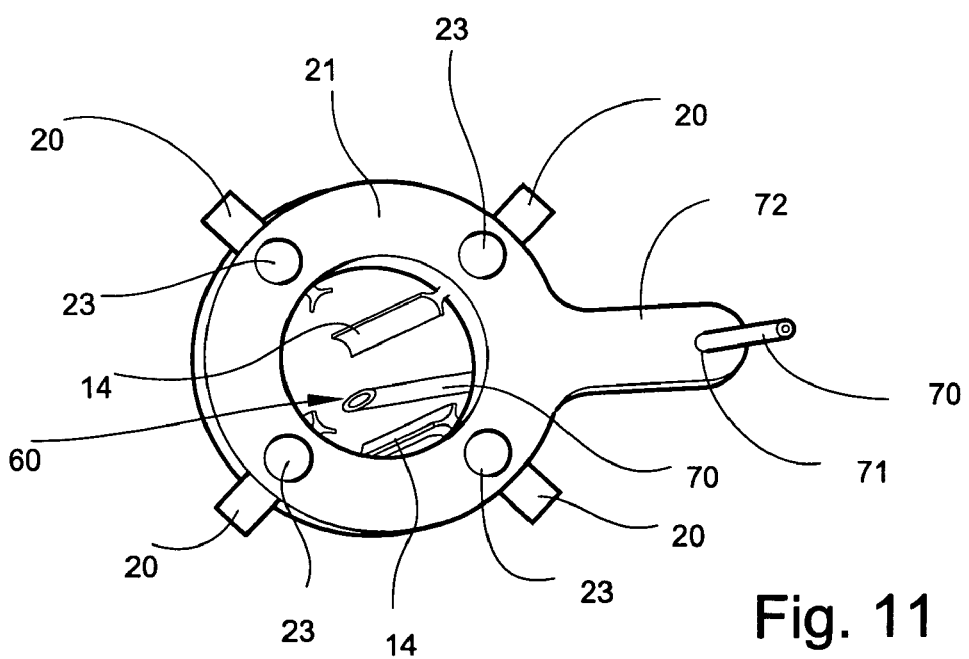
FIG. 11 is a top perspective view of the surgical access device shown in FIG. 10, showing the straight cannula guided through the guide hole so that the tip of the straight cannula is positioned at the periphery of the surgical site, in an embodiment of the present invention.

In another embodiment, as shown in FIGS. 10-11, the mechanism for illuminating the surgical site in a surgical access device 10 of the present invention can comprise a straight insertion cannula, or member 70. The straight insertion cannula member 70 can have a sharp distal tip and a light source 60 attached or integrated at the distal tip. The retainer ring 21 may include a guide slot 71 for receiving and guiding percutaneous insertion of the straight insertion member 70. In an embodiment, the retainer ring 21 can have an arm 72 extending laterally outward in the plane of the retainer ring 21. The guide slot 71 may be included in the retainer ring arm 72, as shown in FIGS. 10-11. The guide slot 71 can have a pre-determined angle for guiding the straight insertion member 70 to the surgical site. The straight insertion cannula member 70 can be guided through the guide slot 71 and inserted percutaneously through the skin and subcutaneous tissue layers via a secondary puncture pathway separate from the surgical access passage, so that the light source 60 at the tip of the straight insertion member 70 can be positioned at a desired location at the periphery of the surgical site.

The retainer ring arm 72 can include one or more guide slot(s) 71, each guide slot 71 having an angle such that the straight insertion member 70 can be guided to the periphery of a surgical site at the distal end of the retractor members 14 of a particular length. Each guide slot 71 can have a different angle to guide the straight insertion member 70 to the precise location at a surgical site, access to which has been created by a different length elongate member 11 and retractor members 14. In an embodiment, the retainer ring 21 can include one or more retainer ring arm(s) 72. Each retainer ring arm 72 can include a differently angled guide slot 71. Alternatively, multiple guide slots 71, each having a different angle, can be included in each retainer ring arm 72. The retainer ring 21 and/or retainer ring arm 72 can include a differently angled guide slot 71 for each length of elongate member 11 and retractor members 14 usable with that retainer ring 21. In an embodiment, the retainer ring 21 can serve as a staging area for other surgical instrument accessories, such as incisor tools or a camera.

The straight insertion member 70 can include an insertion guide 73, for example, indicia, to indicate the distance the straight insertion member 70 has been advanced through the guide slot 71 toward the surgical site. In an embodiment, the insertion guide 73 can be a mechanism, such as a collar (not shown), for stopping advancement of the straight insertion member 70 through the guide slot 71 at selected points along the length of the straight insertion member 70. The insertion guide 73 can be located on the straight insertion member 70 such that when the tip of the straight insertion member 70 is positioned precisely at the desired location at the periphery of the surgical site, the insertion guide 73 may align with the top surface of the retainer ring 21 or arm 72. Insertion guides 73 such as indicia and a collar on the straight insertion member 70 can help a surgeon determine the proper distance for inserting the straight insertion member 70 toward the surgical site and for positioning the distal tip and the light source 60 of the straight insertion member 70 at the desired location at the surgical site.

Figure 12:
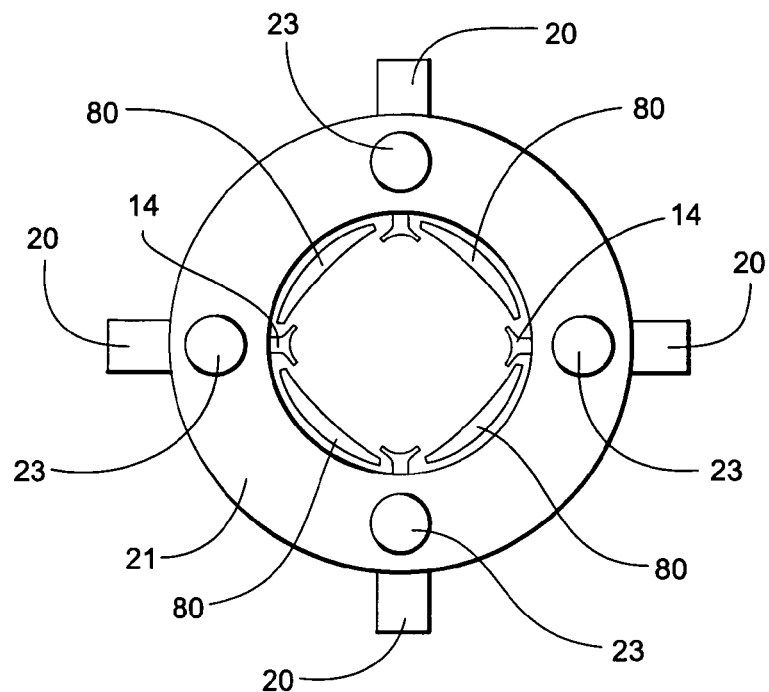
FIG. 12 is a top plan view of the retainer ring shown in FIG. 5, including a set of four secondary retractor members, each including a light source at its distal end, in an embodiment of the present invention.
Figure 13:
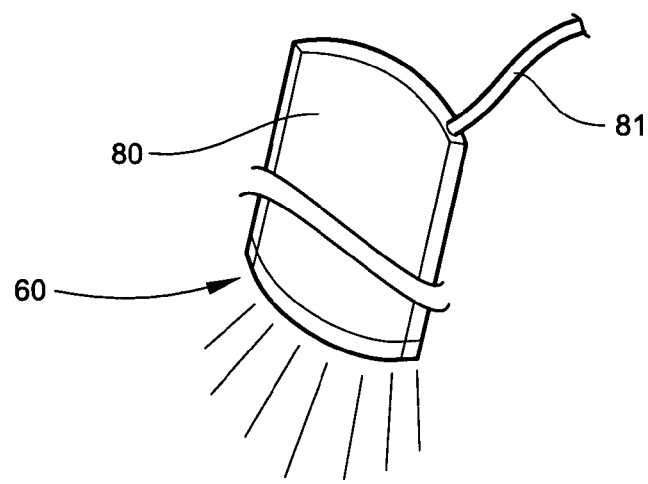
FIG. 13 is a perspective view of one of the secondary retractor members shown in FIG. 12, showing the light source at is distal end, in an embodiment of the present invention.

In another embodiment, the mechanism for illuminating the surgical site in a surgical access device 10 of the present invention can comprise a light source 60 at the distal end 13 of one or more of the plurality of retractor members 14. The light source can be, for example, a light emitting diode (LED), a fiber optic light source, or any suitable source for illuminating a surgical site. In another embodiment, as shown in FIG. 12, the retainer ring 21 can include one or more secondary retractor members 80, each positioned between adjacent retractor members 14. In such an embodiment, the mechanism for illuminating the surgical site can comprise a light source 60 at the distal end of one or more of the secondary retractor member(s) 80. An embodiment of a light source 60 at the distal end of one secondary retractor member 80 is shown in FIG. 13. The light source 60, for example, a fiber optic light source, in a primary retractor member 14 or a secondary retractor member 80 can be powered by a battery inside the retractor member 14, 80 or via a connection 81 to an external power source. The light source 60 at the distal end 13 of the primary retractor member(s) 14 or of the secondary retractor member(s) 80 can provide illumination of the surgical site from the periphery of the site without interfering with access and/or visualization of the site.

In one embodiment, when the primary retractor members 14 are moved radially outward, the secondary retractor members 80 can be moved radially outward as well. Alternatively, the secondary retractor members 80 can be inserted through guide slots or brackets (not shown) in the retainer ring 21 between the retractor member guide channels 22 after the primary retractor members 14 have been moved radially outward. Once in position adjacent the outwardly moved primary retractor members 14, as shown in FIG. 12, the outwardly positioned secondary retractor members 80 can provide additional retraction surface against the tissue being maintained in a retracted position and thus provide added stabilization to the surgical access passage.

Figure 14:
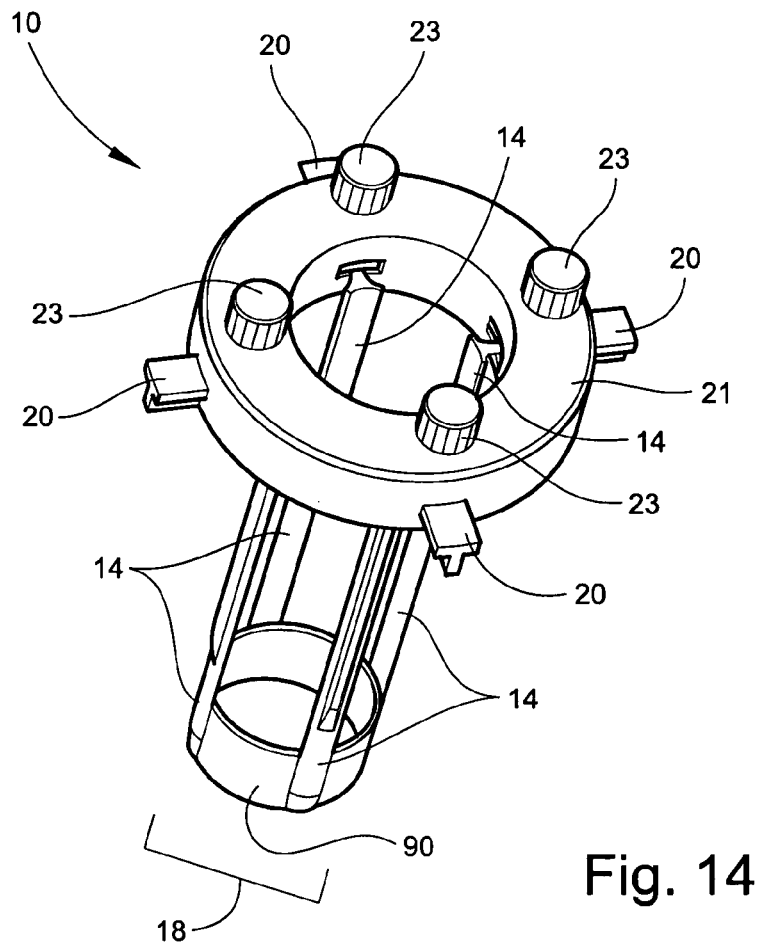
FIG. 14 is a perspective view of the retainer ring and the outwardly moved retractor members as shown in FIG. 4, including a stabilization ring positioned at the distal end of the retractor members in an embodiment of the present invention.

In another embodiment, as shown in FIG. 14, the surgical access device 10 of the present invention can further comprise a stabilization mechanism for stabilizing the retractor members 14 after being moved radially outward. The stabilization mechanism can comprise a stabilization ring 90 positionable inside and along the length of the retractor members 14. Once the retractor members 14 have been moved radially outward by, for example, expanding the expandable body 40 as shown in FIG. 4, and the expandable body 40 is contracted and removed, the stabilization ring 90 can be inserted through the retainer ring 21 inside the retractor members 14. Preferably, the stabilization ring 90 can be positioned near the distal end 13 of the retractor members 14. The stabilization ring 90 can provide rigid support to the inside surfaces 15 of the retractor members 14 for helping to maintain tissue in a retracted position. The stabilization ring 90 can have various dimensions to provide rigid retraction support to the retractor members 14 in various outwardly moved positions, such as the position corresponding to the second, larger cross-sectional dimension 18.

Figures 15A, 15B:
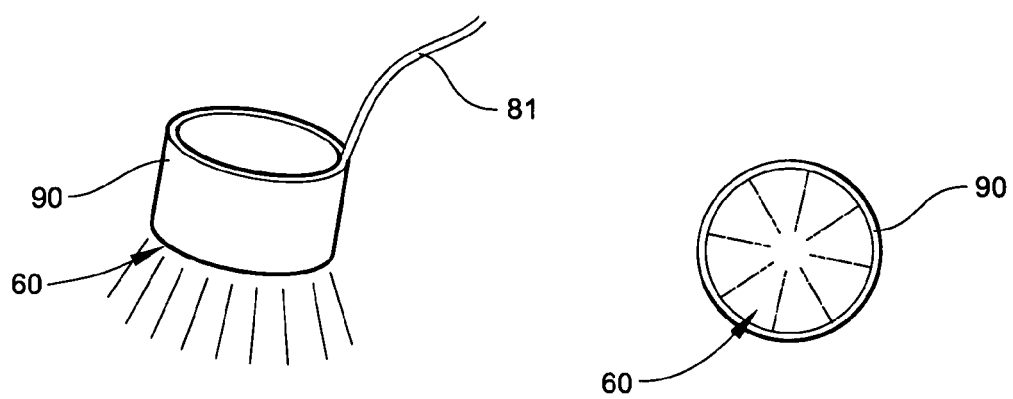
FIG. 15A is a perspective view of the stabilization ring shown in FIG. 14, showing a light source at its distal end, in an embodiment of the present invention.
FIG. 15B is a top view of the stabilization ring shown in FIG. 15A, showing the light source focused below the center of the ring, in an embodiment of the present invention.

As shown in FIGS. 15A and 15B, in such an embodiment, the mechanism for illuminating the surgical site can comprise a light source 60 in the stabilization ring 90. The light source 60 can be connected to an external power supply by a power supply connection 81. Alternatively, the power supply, for example a battery, can be contained within the stabilization ring 90. The light source 60 can provide light in a distal direction from the distal end of the stabilization ring 90 to illuminate a broad portion of the surgical site. Alternatively, as shown in FIG. 15B, the light source 60 can provide light inwardly from the inside surface of the stabilization ring 90 so as to create a concentrated light, or "glow ring" effect, on the surgical site. In an embodiment, the light source 60 in a stabilization ring 90 can provide both a distally-directed light in a broad pattern and a concentrated light toward the center of the surgical site. In an embodiment in which the mechanism for illuminating the surgical site comprises a light source 60 in the stabilization ring 90, illumination of the surgical site from the periphery of the site can be accomplished without interfering with access and/or visualization of the site.

Figure 16:
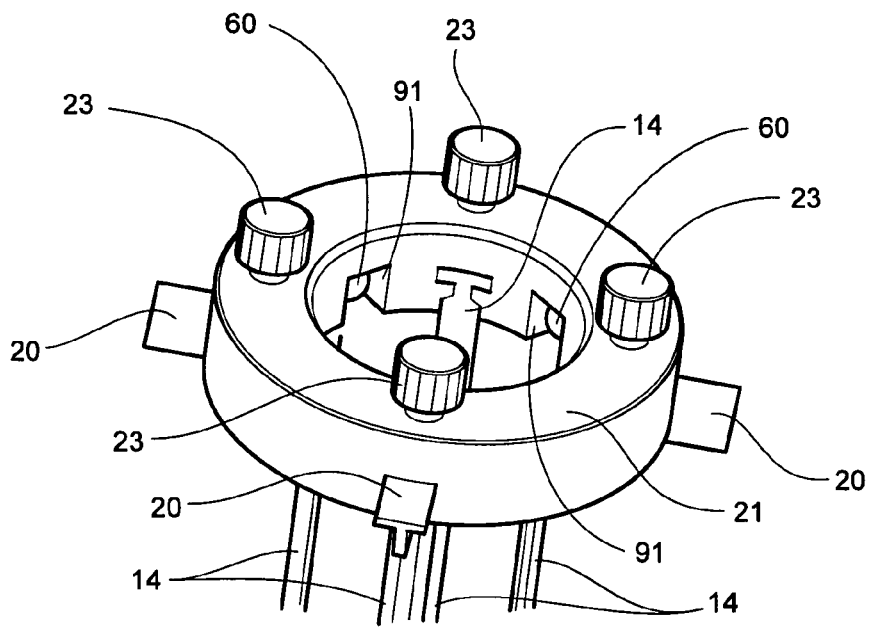
FIG. 16 is a perspective view of the retainer ring shown in FIGS. 4-5, having the retractor members in an outwardly moved position and showing a light source on the distal, or bottom, side under the retainer ring, in an embodiment of the present invention.
Figure 17:
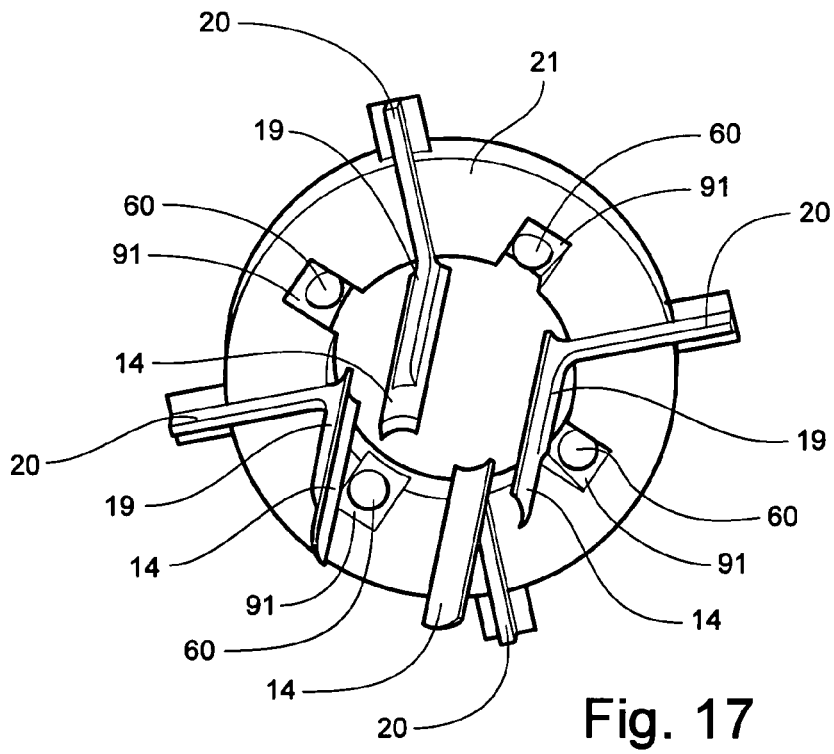
FIG. 17 is a bottom perspective view of the retaining ring shown in FIG. 16, showing four slots on the bottom side of the retaining ring, each slot housing a light source, such as a light emitting diode (LED), in an embodiment of the present invention.

In another embodiment, the mechanism and/or interface for illuminating the surgical site can comprise a light source 60 near an inside edge of the retainer ring 21. Such an embodiment is illustrated in FIGS. 16-17, in which the retractor members 14 are shown in an outwardly moved position. The retainer ring 21 can include one or more recesses 91 (four are shown in FIG. 17) on the bottom side of the retainer ring 21. Each recess 91 can be located between adjacent retractor members 14 and can house a light source 60. In an embodiment, the light source 60 can be attached near the inside edge of the retainer ring 21 without being housed in a recess 91. Each light source 60 can be directed to provide illumination in a different area, for example, in a different quadrant, of the surgical site. The light may converge toward the center of the surgical site. In an embodiment in which the mechanism for illuminating the surgical site comprises a light source 60 in the retainer ring 21, illumination of the surgical site from the periphery of the site can be accomplished without interfering with access and/or visualization of the site.

The light source 60 can be any suitable light source, for example, a light emitting diode (LED). The LED light source, the fiber optic light source, and/or other light sources usable in embodiments of the present invention can include a connection 81 to a power supply and electronic components (not shown) to power, activate, and regulate the light source. Alternatively, the power supply, for example a battery, can be contained within a particular structure of the surgical access device 10.

Some embodiments of the present invention provide advantages over conventional surgical access devices and techniques. For example, using embodiments of devices, systems, kits, and/or methods of the present invention, a surgical access passage can be created and maintained to provide direct access and/or visualization of a surgical site. In such embodiments, surgical access passages having a diameter in the range of about ¾ inch to about 1¼ inches are possible. Such surgical access passage dimensions are an improvement in the amount of direct line of sight to a surgical site as compared to access portals provided by conventional minimally invasive surgical approaches. As a result of such a larger surgical access passage, simultaneous use of a number of surgical instruments under direct visualization at the surgical site is possible. Such instruments include, for example, steerable instruments, shavers, dissectors, scissors, forceps, retractors, dilators, endoscopic surgical instruments, and video cameras.

Some embodiments of the present invention can allow a surgeon to create and maintain a direct visualization surgical access passage using fewer instruments and in less time than in conventional approaches. Conventional approaches can require use of multiple dilators and/or retractors. For example, tissue dilation can require insertion of numerous dilators of increasingly larger diameter before a surgical access passage is large enough to insert a retractor and instruments of a size needed to perform a surgical procedure in an internal body area. In addition, conventional tissue retractors can be bulky, heavy, and difficult to maintain in a given position. In an embodiment of the present invention, the retractor members 14 can be moved outwardly in a one-step process of gradual tissue dilation and secured at various locations along a continuum of cross-sectional dimensions for a surgical access passage. As shown in the embodiments in FIGS. 1-4, the range of cross-sectional areas can include any cross-sectional dimension, or area, between the first cross-sectional dimension 17 of the closed lumen 16 of the elongate member 11 to a cross-sectional dimension equal to the inside diameter of the retainer ring 21.

As an example, if a one-half inch diameter surgical access passage is sufficient, the surgeon can move the retractor members 14 of the elongate member 11 radially outward to create a one-half inch cross-sectional passage. If a one inch diameter surgical access passage is desired, the surgeon can continue to move the retractor members 14 of the elongate member 11 radially outward to create a one inch cross-sectional passage. In this manner, surgical access passages having different cross-sectional dimensions can be created using the same instrument, thereby avoiding the need for more time-consuming, labor-intensive, and equipment-intensive procedures. As such, the range of cross-sectional dimensions of a surgical access passage can be provided from a number of incrementally different dimensions along a continuum of dimensions not limited, for example, by fixed sizes of dilation cannulae. Thus, in embodiments of the present invention, a single surgical access device 10 can be utilized for accessing a surgical site and retracting tissue along a passage from exterior the body to the surgical site, as opposed to separate instruments for accessing and for retracting used in conventional devices and techniques. Such use of fewer instruments to achieve a surgical access passage in less time and an increased capability for direct access and/or visualization of a surgical site can result in fewer surgical risks and less cost for a minimally invasive surgical procedure.

By moving the retractor members 14 of the elongate member 11 in various amounts, the size of a surgical access passage can be customized for the needs of an individual patient's operative site. During tissue retraction, the surgeon can feel when a particular tissue, such as a muscle, is beginning to be over-stretched. Thus, a customized surgical access passage as provided by embodiments of the present invention allows the surgeon to cause less trauma to muscles and other tissues. As a result, the risk of potential complications of a surgical procedure, such as infection and blood loss, can be decreased. Accordingly, post-operative discomfort, healing time, and length of hospital stay can be reduced.

In some embodiments of the present invention, movement of the retractor members 14 can vary. In an embodiment, each retractor member 14 can be moved radially outward from its original closed position that defines the lumen 16 of the elongate member 11. In another embodiment, each of the retractor members 14 can be moved radially outward simultaneously. In still another embodiment, one or more of the retractor members 14 may be moved radially outward more or less than others of the retractor members 14. For example, in an illustrative embodiment of the surgical access device 10 having four retractor members 14, as shown in FIGS. 1-7, two opposing retractor members 14 can be moved radially outward to a first position, such as to a dimension of one-half inch between this first pair of retractor members 14. The two other opposing retractor members 14 can be moved radially outward to a second position, for example, to a dimension of one inch between this second pair of retractor members 14. As such, a surgical access passage having an oval or oblong cross-sectional configuration can be provided. In an embodiment, the surgical access passage created by a surgical access device 10 according to the present invention can comprise a substantially constant cross-sectional dimension from the proximal end 12 of the elongate member 11 exterior the body to the distal end 13 of the elongate member 11 at the surgical site. In such embodiments, surgical access passages having a variety of non-circular cross-sectional configurations can be created. In this manner, the surgeon can create a surgical access passage that is customized to the size and to the shape of the surgical site. A surgical access passage based on the size and shape needed for an individual patient allows the surgeon to traumatize less tissue during the procedure, thus reducing risks of surgical complications such as infection and blood loss, and decreasing discomfort and healing time.

In an embodiment of the present invention, the degree of retraction provided by the surgical access device 10 can be different for different tissue layers. For example, the retractor members 14 can be moved radially outward from a closed position to a first open cross-sectional dimension for the skin, to at least a second open cross-sectional dimension for adipose tissue, and to at least a third open cross-sectional dimension for the remaining tissue in a surgical access passageway. Such variability in tissue retraction can facilitate different surgical access approaches than available with conventional devices and methods.

Some embodiments of the present invention can include a mechanism for illuminating the surgical site that avoids obstructing direct access and/or visualization of the surgical site via the surgical access passage. Thus, embodiments of a surgical access device 10, system, kit, and methods of the present invention can be utilized without the need for a separate viewing element, for example, an optical instrument such as an endoscope. The avoidance of a separate viewing element provides for accurate, more direct visualization of the surgical site, as well as the further advantage of reducing cost over conventional approaches to minimally invasive surgical access.

The present invention includes embodiments of a system useful for creating and maintaining a surgical access passage for the surgical or other treatment of a human or animal. An embodiment of such a system can comprise an elongate member 11 comprising a plurality of retractor members 14 that are moveable radially outward from the first cross-sectional dimension 17 to at least the second, larger cross-sectional dimension 18 in situ (i.e., after the elongate member has been positioned in a patient). The system can further comprise a mechanism and/or interface for moving the retractor members 14 radially outward. The system can further comprise a mechanism and/or interface for guiding the radially outward movement of the retractor members 14 and a mechanism and/or interface for securing each of the retractor members 14 in a range of positions. The system can further comprise a mechanism and/or interface for inserting the elongate member 11 from exterior the body to the surgical site. The system can further comprise a mechanism and/or interface for illuminating the surgical site.

In an illustrative embodiment of a such a system, each of the plurality of retractor members 14 of the elongate member 11 have, as shown in FIG. 2, an inner surface 15 that together define the lumen 16 of the elongate member 11. The closed lumen 16 has a first cross-sectional dimension 17. Each of the retractor members 14 are moveable radially outward from the first cross-sectional dimension 17 of the closed lumen 16 to at least a second, larger cross-sectional dimension 18 for creating a surgical access passage. In an embodiment, the second cross-sectional dimension 18 can be substantially constant between the proximal end 12 and the distal end 13 of the elongate member 11 from exterior the body to the surgical site. In a surgical access passage created by such a system, the passage is capable of receiving instruments and allowing direct access and/or visualization of the surgical site.

The mechanism for guiding the radially outward movement of the retractor members 14 can include a retainer ring 21 having a plurality of retractor member guide channels 22 and configured for placement at the proximal end 12 of and concentric to the plurality of retractor members 14. Each of the retractor members 14 can have a retractor member arm 20 extending outwardly at a substantially 90 degree angle from the proximal end 12 of the retractor member 14, such that each retractor member arm 20 is slidable within one of the guide channels 22. The mechanism for securing each of the retractor members 14 can comprise a wheel lock 23 threaded through a wheel lock guide 24 in the retainer ring 21 into each retainer member guide channel 22. The wheel lock 23 can have adjustable contact with the retainer member arm 20 for securing the retainer member 14 in position in that guide channel 22. Each of the retractor members 14 may be secured in a range of positions, including a first position comprising the first cross-sectional dimension 17, a second position comprising the second cross-sectional dimension 18, and a number of selected positions in between.

In an embodiment of a system, the mechanism for inserting the elongate member 11 from exterior the body to the surgical site can include a stylet 30 comprising a pointed tip 32 and a guide wire bore 33 extending through the stylet 30. The stylet 30 can be inserted into the lumen 16 for guiding the elongate member 11 over a guide wire to the surgical site.

In an embodiment of such a system, the mechanism for moving the retractor members radially outward may be inserted into the lumen 16 and actuated to apply a radially outward force to move the retractor members 14. In one embodiment, the mechanism for moving the retractor members 14 radially outward comprises an expandable body 40. In an alternative embodiment, the mechanism for moving the retractor members radially outward can be a mechanical mechanism or a hydraulic mechanism.

The surgical access passage created by moving the retractor members 14 radially outward in such a system can comprise a cross-sectional dimension from a range of cross-sectional dimensions. Such a range of cross-sectional dimensions can include the first cross-sectional dimension 17 of the lumen 16, a cross-sectional dimension equal to an inside diameter of the retainer ring 21, and any cross-sectional dimension between these two dimensions. For example, the surgical access passage cross-sectional dimension may have a diameter in the range of about ¾ inch to about 1¼ inches. In an embodiment, the surgical access passage cross-sectional dimension may have a diameter less than ¾ inch or more than 1¼ inches. In an embodiment, one or more of the retractor members 14 may be moved radially outward more or less than others of the retractor members 14. In this manner, the surgical access passage may be created having a cross-sectional dimension of a non-circular cross-sectional configuration.

Figure 8:
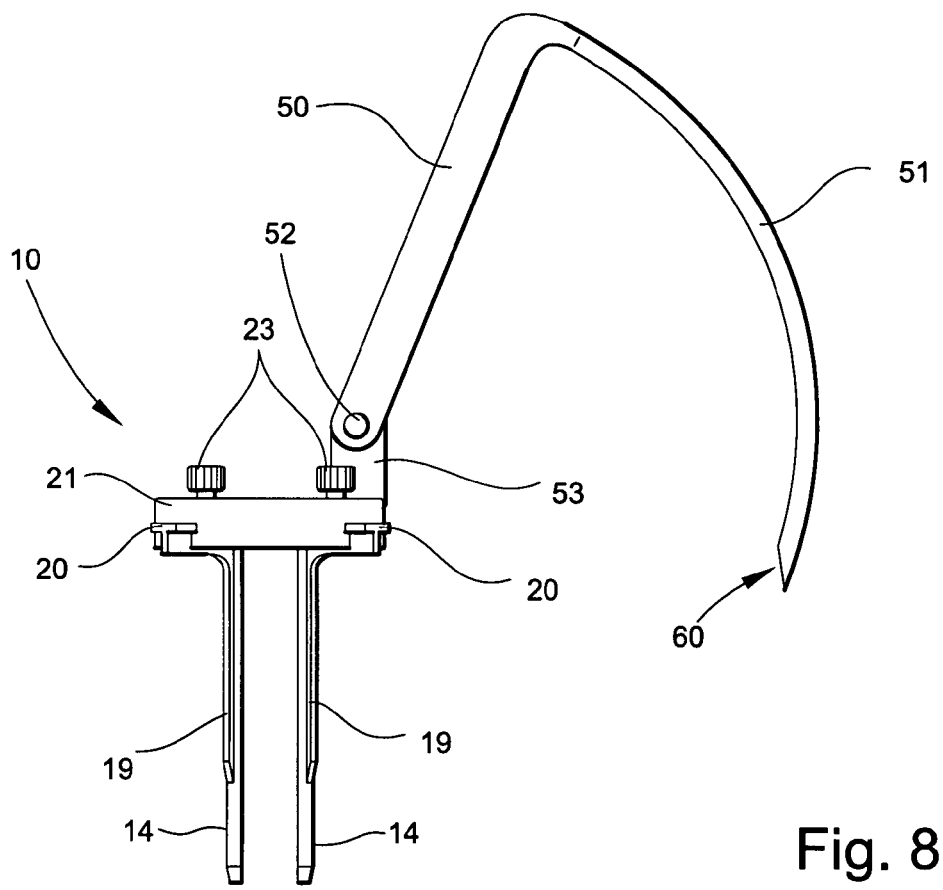
FIG. 8 is a side view of the surgical access device shown in FIGS. 1-4, having a rotatable arm rotatably mounted to the retainer ring and a curved cannula having a sharp tip and carrying a light source attached to the distal end of the rotatable arm in an embodiment of the present invention.

In an embodiment of a system, as shown in FIGS. 8-9, the mechanism for illuminating the surgical site can comprise a rotatable arm 50 rotatably mounted to the retainer ring 21 and a curved insertion member 51 attached to the rotatable arm 50. A light source 60 can be attached or integrated at the distal tip of the curved insertion member 51. The curved insertion member 51 is capable of percutaneous insertion such that the light source 60 at the distal tip of the curved insertion member 51 can be positioned at a desired location at a periphery of the surgical site.

In an embodiment of a system, as shown in FIGS. 10-11, the retainer ring 21 can include a retainer ring arm 72 extending laterally from the retainer ring 21 and having an angled guide slot 71 in the arm 72. The mechanism for illuminating the surgical site can comprise a straight insertion member 70, having a light source 60 attached or integrated at the distal tip of the straight insertion member 70. The straight insertion member 70 is capable of guided percutaneous insertion through the guide slot 71 so that the light source 60 is positionable at a desired location at the periphery of the surgical site. The straight insertion member 70 can include indicia 73 or other mechanism for indicating a distance the insertion member 70 has been inserted toward the surgical site relative to the guide slot 71. Such an insertion guide 73 can aid the surgeon in positioning the distal tip of the straight insertion member 70 and the light source 60 at the desired location at the periphery of the surgical site.

In another embodiment of a system, as shown in FIGS. 12-13, the mechanism for illuminating the surgical site can include a light source 60 at or near the distal end 13 of one or more retractor members 14. In still another embodiment, as shown in FIGS. 16-17, the mechanism for illuminating the surgical site can comprise a light source 60 near an inside edge of the retainer ring 21.

Such a system can further comprise a mechanism for stabilizing the retractor members 14 when the retractor members 14 have been moved radially outward. Such a stabilizing mechanism can be, for example, the stabilizing ring 90, as shown in FIGS. 14, 15A, and 15B. In such an embodiment, the mechanism for illuminating the surgical site can comprise a light source 60 in the stabilization ring 90.

The present invention includes embodiments of a kit comprising the surgical access device 10, as described herein, useful for creating and maintaining a surgical access passage for the surgical or other treatment of a human or animal. An embodiment of such a kit can comprise an elongate member 11 comprising a plurality of retractor members 14 that are moveable radially outward from the first cross-sectional dimension 17 to at least the second, larger cross-sectional dimension 18 after the elongate member 11 has been positioned in a patient. The kit can further comprise a mechanism for moving the retractor members 14 radially outward. The kit can further comprise a mechanism for guiding the radially outward movement of the retractor members 14 and a mechanism for securing each of the retractor members 14 in a range of positions. The kit can further comprise a mechanism for inserting the elongate member 11 from exterior the body to the surgical site. The kit can further comprise a mechanism for illuminating the surgical site.

In some embodiments, a kit can comprise various combinations of these and/or other elements. For example, in one embodiment, a kit can include the elongate member 11, the mechanism for moving the retractor members 14 radially outward, the mechanism for guiding the radially outward movement of the retractor members 14, and the mechanism for securing the retractor members 14 in a range of positions. In this embodiment, the kit may or may not include the mechanism for inserting the elongate member 14 from exterior the body to the surgical site. For example, if it is preferred that the components of the kit are reusable except for the stylet 30 for inserting the elongate member 11 from exterior the body to the surgical site, a disposable stylet 30 may be provided separately. In another embodiment, such a kit can include multiple or alternative mechanisms for illuminating the surgical site.

In an illustrative embodiment of a such a kit, each of the plurality of retractor members 14 of the elongate member 11 have, as shown in FIG. 2, an inner surface 15 that together define the lumen 16 of the elongate member 14. The closed lumen 16 has a first cross-sectional dimension 17. Each of the retractor members 14 are moveable radially outward from the first cross-sectional dimension 17 of the closed lumen 16 to at least a second, larger cross-sectional dimension 18 for creating a surgical access passage. In an embodiment, the second cross-sectional dimension 18 can be substantially constant between the proximal end 12 and the distal end 13 of the elongate member 11 from exterior the body to the surgical site. In a surgical access passage created by the surgical access device 10 in such a kit, the passage is capable of receiving instruments and allowing direct access and/or visualization of the surgical site.

In an embodiment of a kit, the mechanism for guiding the radially outward movement of the retractor members 14 can include a retainer ring 21 having a plurality of retractor member guide channels 22 and configured for placement at the proximal end 12 of and concentric to the plurality of retractor members 14. Each of the retractor members 14 can have a retractor member arm 20 extending outwardly at a substantially 90 degree angle from the proximal end 12 of the retractor member 14, such that each retractor member arm 20 is slidable within one of the guide channels 22. The mechanism for securing each of the retractor members 14 can comprise a wheel lock 23 threaded through a wheel lock guide 24 in the retainer ring 21 into each retainer member guide channel 22. The wheel lock 23 can have adjustable contact with the retractor member arm 20 for securing the retractor member 14 in position in that guide channel 22. Each of the retractor members 14 may be secured in a range of positions, including a first position comprising the first cross-sectional dimension 17, a second position comprising the second cross-sectional dimension 18, and a number of selected positions in between.

In an embodiment of a kit, the mechanism for inserting the elongate member 11 from exterior the body to the surgical site can comprise a stylet 30 comprising a pointed tip 32 and a guide wire bore 33 extending through the stylet 30. The stylet 30 can be inserted into the lumen 16 for guiding the elongate member 11 over a guide wire to the surgical site.

In an embodiment of a kit, the mechanism for moving the retractor members 14 radially outward may be inserted into the lumen 16 and actuated to apply a radially outward force to move the retractor members 14. In one embodiment, the mechanism for moving the retractor members 14 radially outward comprises an expandable body 40. In an alternative embodiment, the mechanism for moving the retractor members 14 radially outward can be a mechanical mechanism or a hydraulic mechanism.

The surgical access passage created by moving the retractor members 14 radially outward with the surgical access device 10 in such a kit can comprise a cross-sectional dimension from a range of cross-sectional dimensions. Such a range of cross-sectional dimensions can include the first cross-sectional dimension 17 of the lumen 16, a cross-sectional dimension equal to an inside diameter of the retainer ring 21, and any cross-sectional dimension between these two dimensions. In an embodiment, one or more of the retractor members 14 may be moved radially outward more or less than others of the retractor members 14. In this manner, the surgical access passage may be created having a cross-sectional dimension of a non-circular cross-sectional configuration.

In an embodiment of a kit, as shown in FIGS. 8-9, the mechanism for illuminating the surgical site can comprise a rotatable arm 50 rotatably mounted to the retainer ring 21 and a curved insertion member 51 attached to the rotatable arm 50. A light source 60 can be attached or integrated at the distal tip of the curved insertion member 51. The curved insertion member 51 is capable of percutaneous insertion such that the light source 60 at the distal tip of the curved insertion member 51 can be positioned at a desired location at a periphery of the surgical site.

In an embodiment of a kit, as shown in FIGS. 10-11, the retainer ring 21 can include a retainer ring arm 72 extending laterally from the retainer ring 21 and having an angled guide slot 71 in the arm 72. The mechanism for illuminating the surgical site can comprise a straight insertion member 70, having a light source 60 attached or integrated at the distal tip of the straight insertion member 70. The straight insertion member 70 is capable of guided percutaneous insertion through the guide slot 71 so that the light source 60 is positionable at a desired location at the periphery of the surgical site. The straight insertion member 70 can include indicia 73 or other mechanism for indicating a distance the insertion member 70 has been inserted toward the surgical site relative to the guide slot 71. Such an insertion guide 73 can aid the surgeon in positioning the distal tip of the straight insertion member 70 and the light source 60 at the desired location at the periphery of the surgical site.

In another embodiment of a kit, as shown in FIGS. 12-13, the mechanism for illuminating the surgical site can include a light source 60 at or near the distal end 13 of one or more retractor members 14. In still another embodiment, as shown in FIGS. 16-17, the mechanism for illuminating the surgical site can comprise a light source 60 near an inside edge of the retainer ring 21.

Such a kit can further comprise a mechanism for stabilizing the retractor members 14 when the retractor members 14 have been moved radially outward. Such a stabilizing mechanism can be, for example, the stabilization ring 90, as shown in FIGS. 14, 15A, and 15B. In such an embodiment, the mechanism for illuminating the surgical site can comprise a light source 60 in the stabilization ring 90.

Some embodiments of the present invention can include methods for manufacturing the devices, systems, and kits of the present invention. For example, the surgical access device 10 of the present invention can be made from stainless steel or other surgical-grade materials or plastics. Components of the surgical access device 10, system, and kit according to the present invention may be made of a material having sufficient strength and durability to perform expected functions in various surgical procedures. For example, the retractor members 14 may preferably be made of a material sufficiently strong to separate planes of tissue of various types. All or portions of such a surgical access device 10, system, and kit can be designed for reuse after sterilization or can be disposable after a single use. For example, in one embodiment, the elongate member 11, the mechanism for guiding the radially outward movement of the retractor members 14 (such as the retainer ring 21), the mechanism for securing the retractor members 14 in a range of positions (such as the wheel locks 23), and the mechanism for illuminating the surgical site can be made for reuse. In such an embodiment, the mechanism for moving the retractor members 14 radially outward (such as the expandable body 40) and the mechanism for inserting the elongate member 11 from exterior the body to the surgical site (such as the stylet 30) may be made as disposable components.

Figure 18:
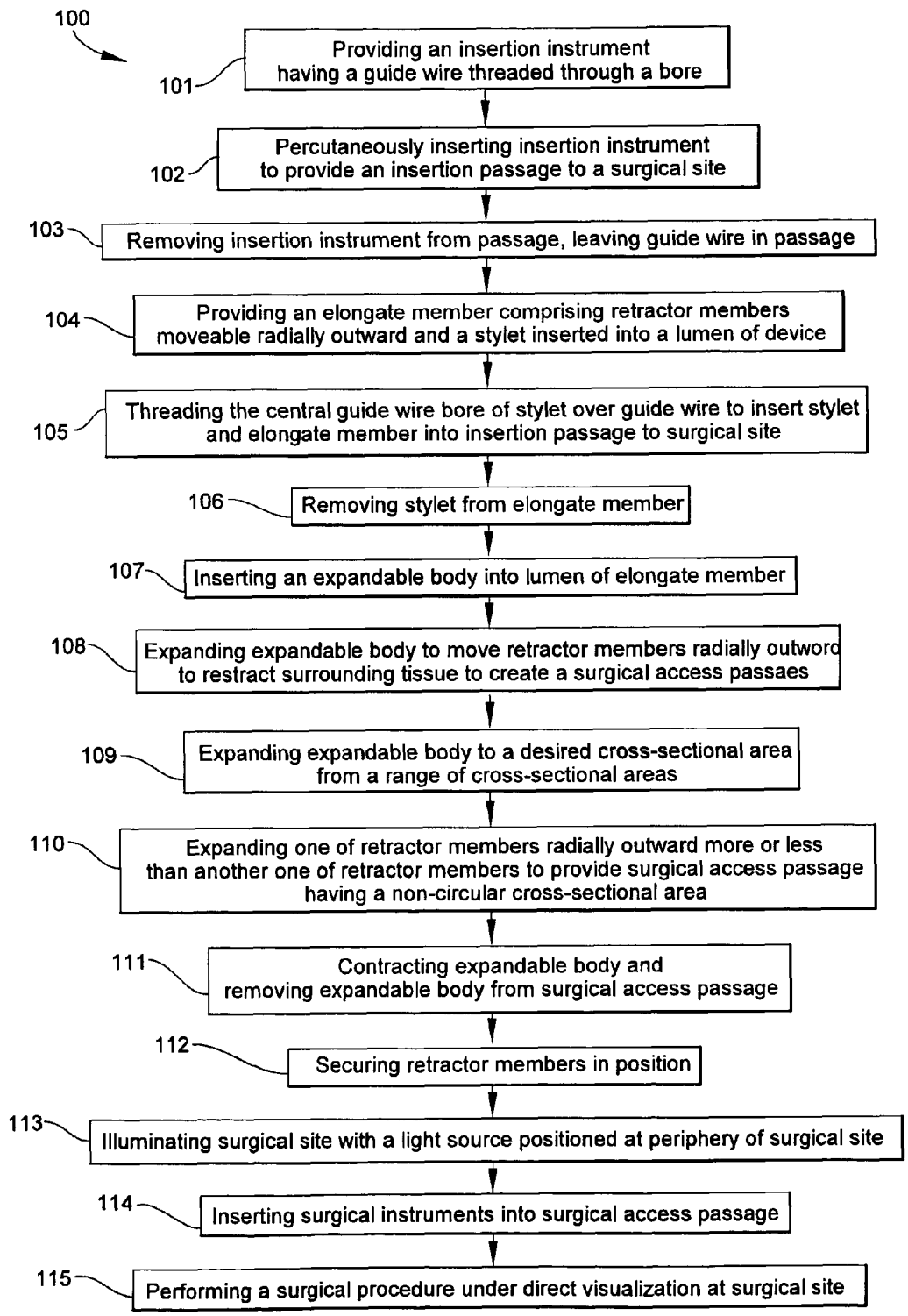
FIG. 18 is a flow chart illustrating steps for creating a surgical access passage in an embodiment of a method of the present invention.

Some embodiments of the present invention can include methods for creating a surgical access passage in order to access a surgical site for the surgical or other treatment of a human or animal. FIG. 18 illustrates an embodiment of a such a method 100. In such an embodiment, the surgical access device 10, as described herein, may be provided (104). A plurality of retractor members 14 of an elongate member 11 in such a surgical access device 10 can be moved radially outward from the first cross-sectional dimension 17 to at least the second, larger cross-sectional dimension 18 after the elongate member 11 has been positioned in a patient. Movement of the retractor members 14 can be guided radially outward. The method can further include securing each of the retractor members 14 in a range of positions (112). The method can further include steps for inserting the elongate member 11 from exterior the body to the surgical site (101-103, 105-106). The method can further include illuminating the surgical site (113). In a surgical access passage created by such methods, the second cross-sectional dimension 18 can be substantially constant between the proximal end 12 and the distal end 13 of the elongate member 11 from exterior the body to the surgical site. In a surgical access passage created by such a method, the passage may be capable of receiving instruments and allowing direct access and/or visualization of the surgical site.

An illustrative embodiment of a method for creating a surgical access passage can include providing (104) an elongate member 11 comprising a proximal end 12, a distal end 13, and a plurality of retractor members 14. Each of the retractor members 14 can have an inner surface 15 that together define a lumen 16 of the elongate member 11 having the first cross-sectional dimension 17. The elongate member 11 can be percutaneously inserted (105) to a surgical site through a stab wound or small incision made in a patient's skin above the targeted site. Once the elongate member 11 is in a desired position adjacent the surgical site, the expandable body 40 can be inserted (107) into the lumen 16 of the elongate member 11 and expanded (108, 109) to move each of the plurality of retractor members 14 radially outward to at least the second cross-sectional dimension 18. The expandable body 40 can then be contracted and removed (111) from the surgical access passage.

In such an embodiment, percutaneous insertion of the elongate member 11 to the surgical site can further include first percutaneously inserting (102) an insertion instrument (not shown) to provide an insertion passage to the surgical site. The insertion instrument can be a small cannula having a sharp tip, for example, a trocar cannula. The insertion instrument can comprise a guide wire bore and a guide wire threaded through the guide wire bore (101). Once the insertion instrument has been inserted (102) to the surgical site to create an insertion passage, it can be removed, while leaving the guide wire in the insertion passage (103). In an embodiment, the stylet 30 comprising a pointed tip 32 and a guide wire bore 33 extending through the stylet 30 can be inserted (104) into the lumen 16 of the elongate member 11. The stylet 30 and elongate member 11 can then be inserted through the insertion passage to the surgical site by threading (105) the stylet guide wire bore 33 over the guide wire. After the elongate member 11 is in position, the stylet 30 and guide wire can be removed (106) from the lumen 16 of the elongate member 11. Alternatively, the insertion instrument can be placed directly in the lumen 16 of the elongate member 11, without the stylet 30, and the insertion instrument and elongate member 11 inserted together to the surgical site.

In another embodiment, the insertion instrument utilized to create an initial percutaneous route, or insertion passage, to the surgical site can be a Jamshidi needle (not shown). The elongate member 11 can be threaded directly over the Jamshidi needle to the surgical site. When the elongate member 11 is in a desired position, the Jamshidi needle can be removed from the elongate member 11.

In an embodiment of such methods, each of the retractor members 14 may be secured (112) in a range of positions including a position comprising the first cross-sectional dimension 17, a position comprising the second cross-sectional dimension 18, and any cross-sectional dimension in between. For example, a retainer ring 21 can be positioned at the proximal end 12 and concentric to the plurality of retractor members 14. The retainer ring 21 may be placed in a resting position on the patient's skin encircling the surgical access passage formed by insertion of the elongate member 11. Each of the retractor members 14 can have a retractor member arm 20 extending outwardly at a substantially 90 degree angle from the proximal end 12 of the retractor member 14. The retainer ring 21 can include a plurality of retractor member guide channels 22, and each retractor member arm 20 can be positioned so as to be slidable within one of the guide channels 22.

In such an arrangement, as the retractor members 14 move radially outward, each of the retractor member arms 20 can slide outwardly through the retractor member guide channels 22. The retractor member arms 20 can be secured with a threaded wheel lock 23 adjustably inserted through the retainer ring 21 into each guide channel 22 into securing contact with the retractor member arm 20 positioned therein. The expandable body 40 can be expanded (109) to one cross-sectional dimension from a range of cross-sectional dimensions between the first cross-sectional dimension 17 of the lumen 16 and a cross-sectional dimension equal to an inside diameter of the retainer ring 21. Movement of the retractor members 14 radially outward with the expandable body 40 causes surrounding tissue to be retracted (108), thereby creating a surgical access passage inside the outwardly moved retractor members 14. When the expandable body 40 has been expanded and the retractor members 14 are in position corresponding to a desired cross-sectional dimension, the wheel locks 23 can be adjusted downward through the matingly threaded wheel lock guides 24 to secure the retractor member arms 20 and retractor members 14 in that position. Then, the expandable body 40 can be contracted and removed (111) from the elongate member 11. In this manner, a surgical access passage can be created and maintained for direct access and/or visualization of the surgical site.

The surgical access passage created in such methods can comprise a substantially constant cross-sectional dimension between the proximal end 12 of the elongate member 11 exterior the body and the distal end 13 of the elongate member 11 at the surgical site. Such a surgical access passage can comprise a cross-sectional dimension having a diameter in the range of about ¾ inch to about 1¼ inches. In embodiments, the surgical access passage cross-sectional dimension may have a diameter less than ¾ inch or greater than 1¼ inches, as the surgical approach may dictate or as the surgical procedure may require. In an embodiment of a method, one of the retractor members 14 may be moved radially outward more or less than another one of the retractor members 14 to provide the surgical access passage having a non-circular cross-sectional configuration (110).

An embodiment of a method for creating a surgical access passage can further include illuminating (113) the surgical site with a light source (for example, a LED light or a fiber optic light) 60 positioned at a periphery of the surgical site. In an embodiment, the mechanism for illuminating the surgical site may be positioned exterior of the elongate member 11. For example, the mechanism for illuminating the surgical site can be configured for operation at the distal end of a separate cannula 51, 70. The separate cannula 51, 70 may be capable of guided percutaneous insertion through a second puncture pathway to the surgical site for positioning the light source 60 at the periphery of the surgical site. In an alternative embodiment, the mechanism for illuminating the surgical site may be positioned within the interior of the elongate member 11. For example, the mechanism for illuminating the surgical site can be provided on the retractor members 14, the inner (distal) face of the retainer ring 21, and/or on a stabilization mechanism positionable inside the outwardly moved retractor members 14. In such embodiments, the surgical access passage is free from obstruction by the mechanism for illuminating the surgical site.

An embodiment of a method for creating a surgical access passage can further comprise inserting a plurality of surgical instruments into the surgical access passage (114). An embodiment of a method can further comprise performing a surgical procedure under direct access and/or visualization of the surgical site (115).

The devices, systems, kits, and methods embodying the present invention can be adapted for use in many suitable interior body regions and types of surgical procedures in humans and animals, wherever access for direct access and/or visualization of a surgical site may be desired for a therapeutic or diagnostic purpose. The illustrative embodiments are described in association with devices, systems, kits, and methods used to treat bones. For example, the surgical site can be a spine or a joint. In other embodiments, the present invention may be used in other interior body regions or types of tissue.

Although the present invention has been described with reference to particular embodiments, it should be recognized that these embodiments are merely illustrative of the principles of the present invention. Those of ordinary skill in the art will appreciate that a surgical access device, systems, kits, and methods for making and using a surgical access device for performing minimally invasive surgery may be constructed and implemented in other ways and embodiments. In addition, where methods and steps described above indicate certain events occurring in a particular order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above. Accordingly, the description herein should not be read as limiting the present invention, as other embodiments also fall within the scope of the present invention.

What is claimed is:

1. A method of creating a surgical access passage, comprising:
percutaneously inserting to a surgical site an elongate member comprising a proximal end, a distal end, and a plurality of retractor members each having an inner surface that together define a lumen of the elongate member, the lumen having a first cross-sectional dimension that is substantially constant between the proximal end and the distal end of the elongate member, wherein the inner surfaces of the retractor members are positioned around a stylet in an insertion configuration in which the stylet also includes a proximal portion extending proximally from the proximal end of the elongate member and a distal end extending distally from the distal end of the elongate member, wherein percutaneously inserting the elongate member includes guiding the stylet and elongate member in the insertion configuration to position the distal end of the elongate member at the surgical site so that the lumen of the elongate member provides the surgical access passage to the surgical site when the stylet is removed from the lumen;
removing the stylet from the lumen of the elongate member after percutaneously inserting the elongate member;

inserting an expandable body into the lumen of the elongate member after removing the stylet, wherein the expandable body has a length that is substantially the same as a length of the elongate member from the proximal end to the distal end of the elongate member;

expanding the expandable body along the length of the expandable body to move the plurality of retractor members radially outward to any second cross-sectional dimension on a continuum that is equal to or less than a maximum cross-sectional dimension, wherein the plurality of retractor members move simultaneously away from one another so that the second cross-sectional dimension of the lumen is substantially constant from the proximal end to the distal end of the elongate member and expansion of the expandable body provides gradual tissue dilation along the length of the elongate member as the plurality of retractor members move radially outward; and contracting the expandable body and removing the expandable body from the surgical access passage.

2. The method of claim 1, wherein percutaneously inserting the elongate member further comprises:

providing an insertion instrument having a guide wire bore and a guide wire threaded through the guide wire bore;

percutaneously inserting the insertion instrument to provide an insertion passage to the surgical site;

removing the insertion instrument from the insertion passage, while leaving the guide wire in the insertion passage;

the stylet comprising a stylet guide wire bore extending through the stylet; and threading the stylet guide wire bore over the guide wire to insert the stylet and the elongate member into the insertion passage to the surgical site.

3. The method of claim 1, further comprising securing the retractor members in a position comprising the first cross-sectional dimension or in a position comprising the second cross-sectional dimension.

4. The method of claim 3, further comprising a retractor member arm extending outwardly from the proximal end of each retractor member, the method further comprising placing a retainer ring comprising a plurality of retractor member guide channels at the proximal end of and concentric to the plurality of retractor members, each retractor member arm positioned and slidable within one of the guide channels, wherein securing the retractor members further comprises securing each of the retractor member arms with a threaded wheel lock adjustably inserted through the retainer ring into each guide channel into securing contact with the retractor member arm positioned therein.

5. The method of claim 1, further comprising placing a retainer ring at the proximal end and concentric to the plurality of retractor members after percutaneously inserting the elongate member to the surgical site, wherein expanding the expandable body further comprises expanding the expandable body to one cross-sectional dimension from a range of cross-sectional dimensions between the first cross-sectional dimension of the lumen and the maximum cross-sectional dimension which is equal to an inside diameter of the retainer ring.

6. The method of claim 1, wherein the surgical access passage comprises a substantially constant cross-sectional dimension between the proximal end exterior a body and the distal end at the surgical site.

7. The method of claim 1, wherein the surgical access passage comprises a cross-sectional dimension having a diameter in the range of ¾ inch to 1¼ inch.

8. The method of claim 1, further comprising moving one of the retractor members radially outward more or less than another one of the retractor members to provide the surgical access passage having a non-circular cross-sectional configuration after moving the plurality of retractor members radially outward to the second cross-sectional dimension.

9. The method of claim 1, further comprising illuminating the surgical site with a light source positioned at a periphery of the surgical site.

10. The method of claim 1, further comprising inserting a plurality of surgical instruments into the surgical access passage.

11. The method of claim 1, further comprising performing a surgical procedure under direct visualization of the surgical site.

12. The method of claim 1, wherein the surgical site comprises a spine.

13. The method of claim 1, wherein the surgical site comprises a joint.

* * * * *